United States Patent [19]

Demerson et al.

[11] 4,273,773
[45] Jun. 16, 1981

[54] ANTIHYPERTENSIVE TRICYCLIC ISOINDOLE DERIVATIVES

[75] Inventors: Christopher A. Demerson, Montreal; Leslie G. Humber, Dollard des Ormeaux; Jean-Marie Ferland, St. Laurent, all of Canada

[73] Assignee: American Home Products Corporation, New York, N.Y.

[21] Appl. No.: 78,547

[22] Filed: Sep. 24, 1979

[51] Int. Cl.³ .................. A61K 31/495; C07D 241/36
[52] U.S. Cl. ........................ 424/250; 260/325 PH; 424/251; 544/246; 544/252; 544/343; 544/344
[58] Field of Search ........................ 544/344; 424/250

[56] References Cited

U.S. PATENT DOCUMENTS

| 3,557,120 | 1/1971 | Archer et al. | 544/344 |
| 3,597,422 | 8/1971 | Winn | 260/268 TR |
| 3,853,879 | 12/1974 | Freed et al. | 544/344 |

OTHER PUBLICATIONS

M. Machida et al., Chem. Abstracts 88:50823h (1978).
M. Winn et al., J. Org. Chem., 34, 249 (1969).
M. Winn et al., J. Org. Chem., 33, 3779 (1968).

*Primary Examiner*—Anton H. Sutto
*Assistant Examiner*—M. C. Eakin
*Attorney, Agent, or Firm*—Arthur E. Wilfond

[57] ABSTRACT

Tricyclic isoindole derivatives characterized by having a 1,2,3,4,6,10b-hexahydropyrazino[2,1-a]isoindole or 1,3,4,10b-tetrahydropyrimido[6,1-a]isoindol-6(2H)-one nucleus are disclosed. The foregoing compounds are useful antihypertensive agents.

52 Claims, No Drawings

ANTIHYPERTENSIVE TRICYCLIC ISOINDOLE DERIVATIVES

RELATED CASE

Certain compounds used as intermediates herein are disclosed in 1,3-DIHYDRO-3-(2-HYDROXYETHYL)-2H-ISOINDOL-1-ONE DERIVATIVES Ser. No. 78,546 of Wilbur Lippmann, Christopher A. Demerson, Jean-Marie Ferland and Leslie G. Humber, filed on even date herewith. Application Ser. No. 78,548 of Wilbur Lippmann, METHOD OF USE AND COMPOSITION FOR 1,3-DIHYDRO-3-(2-HYDROXY-2-METHYLPROPYL)-2H-ISOINDOL-1-ONE, filed on even date herewith also is related thereto.

BACKGROUND OF THE INVENTION (a) Field of the Invention

This invention relates to novel tricyclic isoindole derivatives, to useful intermediates, to processes for their preparation and to therapeutically acceptable acid addition salts and pharmaceutical compositions of the derivatives.

More specifically, the present invention relates to novel 1,2,3,4,6,10b-hexahydropyrazino[2,1-a] isoindole and 1,3,4,10b-tetrahydropyrimido[6,1-a] isoindol-6(2H)-one derivatives possessing valuable pharmacologic properties. These derivatives are useful for treating hypertension in mammals.

(b) Description of the Prior Art

Compounds having the tricyclic isoindole nucleus are known. For example, compounds having the pyrazino[2,1-a] isoindole nucleus are disclosed by M. Winn in U.S. Pat. No. 3,597,422, issued Aug. 3, 1971. This patent discloses 1,1-dimethyl-6-phenyl-1,2,3,4-tetrahydropyrazino[2,1-a]isoindole derivatives useful as fungicides.

Compounds having the pyrimido[6,1-a]isoindole nucleus have not been reported previously. However, isomeric pyrimidoisoindoles, for example, pyrimido[2,1-a]isoindoles, have been disclosed; for example, M. Winn and H. E. Zaugg, J. Org. Chem., 34, 249 (1969). The latter reference and M. Winn and H. E. Zaugg, J. Org. Chem., 33. 3779 (1968) are cited in U.S. Pat. No. 3,597,422, noted above.

SUMMARY OF THE INVENTION

The compounds of this invention are represented by formula I

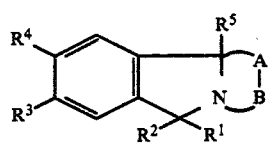

in which $R^1$ is hydrogen; $R^2$ is hydrogen, hydroxy or hydroxymethyl, or $R^1$ and $R^2$ together form a ketone; $R^3$ and $R^4$ each is hydrogen, lower alkoxy, lower alkyl, trifluoromethyl, halo or hydroxy, or $R^3$ and $R^4$ together form a $OCH_2O$ chain; $R^5$ is hydrogen, lower alkyl or phenylmethyl; and A-B is a chain of formula $CHR^6NR^7CR^8R^9CR^{10}R^{11}$ wherein $R^6$ is hydrogen or lower alkyl; $R^7$ is hydrogen, lower alkyl, lower alkanoyl, cyclohexylcarbonyl, phenylmethyl, benzoyl, carboxymethyl, aminocarbonyl, 4-nitrobenzoyl, 4-aminobenzoyl, a radical of formula $(CH_2)_nNR^{12}R^{13}$ wherein n is an integer from two to six, and $R^{12}$ and $R^{13}$ each is hydrogen or lower alkyl, or a radical of formula $CO(CH_2)_{n-1}NR^{12}R^{13}$ wherein n, $R^{12}$ and $R^{13}$ are as defined herein; $R^8$, $R^9$, $R^{10}$ and $R^{11}$ each is hydrogen or lower alkyl; or $R^9$ and $R^{10}$ together form a $(CH_2)_4$ chain, and the carbon atom bearing $R^{10}$ and $R^{11}$ is attached to the nitrogen atom of formula I; or A-B is a chain of formula $CH_2CR^{14}R^{15}NR^{16}CHR^{17}$ wherein $R^{14}$ and $R^{15}$ each is hydrogen or lower alkyl; $R^{16}$ is hydrogen, a radical of formula $(CH_2)_n NR^{12}R^{13}$ wherein n, $R^{12}$ and $R^{13}$ are as defined herein or a radical of formula $CO(CH_2)_{n-1} NR^{12}R^{13}$ wherein n, $R^{12}$ and $R^{13}$ are as defined herein, and $R^{17}$ is hydrogen, or $R^{16}$ and $R^{17}$ together form an imine; and the carbon atom bearing $R^{17}$ is attached to the nitrogen atom of formula I; with the proviso that when $R^1$ is hydrogen, $R^2$ is hydrogen, hydroxy or hydroxymethyl, or $R^5$ is lower alkyl or phenylmethyl, then A-B is a chain of formula $CHR^6NR^7CR^8R^9CR^{10}R^{11}$ wherein $R^6$, $R^7$, $R^8$, $R^9$, $R^{10}$ and $R^{11}$ are as defined herein and with the additional proviso that when A-B is a chain of formula $CHR^6NR^7CR^8R^9CR^{10}R^{11}$ wherein $R^6$ is lower alkyl then $R^1$, $R^2$, $R^5$, $R^8$ and $R^9$ are hydrogen, or $R^1$ and $R^2$ together form a ketone.

A preferred group of compounds of formula I are represented by formula Ia

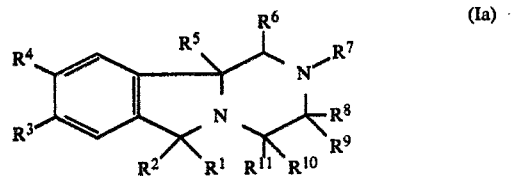

in which $R^1$ is hydrogen; $R^2$ is hydrogen, hydroxy or hydroxymethyl, or $R^1$ and $R^2$ together form a ketone; $R^3$ and $R^4$ each is hydrogen, lower alkoxy, lower alkyl, trifluoromethyl, halo or hydroxy; or $R^3$ and $R^4$ together form a $OCH_2O$ chain; $R^5$ is hydrogen, lower alkyl or phenylmethyl; $R^6$ is hydrogen or lower alkyl; $R^7$ is hydrogen, lower alkyl, lower alkanoyl, cyclohexylcarbonyl, phenylmethyl, benzoyl, carboxymethyl, aminocarbonyl, 4-nitrobenzoyl, 4-aminobenzoyl, a radical of formula $(CH_2)_nNR^{12}R^{13}$ wherein n is an integer from two to six, and $R^{12}$ and $R^{13}$ each is hydrogen or lower alkyl, or a radical of formula $CO—(CH_2)_{n-1}NR^{12}R^{13}$ wherein n, $R^{12}$ and $R^{13}$ are as defined herein; $R^8$, $R^9$, $R^{10}$ and $R^{11}$ each is hydrogen or lower alkyl; or $R^9$ and $R^{10}$ together form a $(CH_2)_4$ chain; with the proviso that when $R^6$ is lower alkyl then $R^1$, $R^2$, $R^5$, $R^8$ and $R^9$ are hydrogen; or $R^1$ and $R^2$ together form a ketone.

A preferred group of compounds of formula Ia are those in which $R^1$ and $R^{11}$ are hydrogen; $R^2$ is hydrogen or hydroxymethyl; or $R^1$ and $R^2$ together form a ketone; $R^3$ and $R^4$ each is hydrogen, lower alkoxy, lower alkyl, halo or hydroxy; $R^5$ is hydrogen, lower alkyl or phenylmethyl; $R^6$ is hydrogen or lower alkyl; $R^7$ is hydrogen, lower alkyl, lower alkanoyl, cyclohexylcarbonyl, phenylmethyl, benzoyl, 4-nitrobenzoyl, 4-aminobenzoyl, a radical of formula $(CH_2)_nNR^{12}R^{13}$ wherein n is an integer from two to six, and $R^{12}$ and $R^{13}$ each is lower alkyl, or a radical of formula $CO—(CH_2)_{n-1}NR^{12}R^{13}$ wherein n is an integer from two to six, and $R^{12}$ and $R^{13}$ each is lower alkyl; $R^8$, $R^9$ and $R^{10}$ each is hydrogen or lower alkyl; with the proviso that when $R^6$ is lower alkyl then $R^1$, $R^2$, $R^5$, $R^8$ and $R^9$ are hydrogen or $R^1$ and $R^2$ together form a ketone.

Another preferred group of compounds of formula I are represented by formula Ib

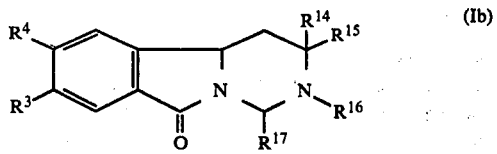

in which $R^3$ and $R^4$ each is hydrogen, lower alkoxy, lower alkyl, trifluoromethyl, halo, or hydroxy; or $R^3$ and $R^4$ together form a OCH$_2$O chain; $R^{14}$ and $R^{15}$ each is hydrogen or lower alkyl; $R^{16}$ is hydrogen, a radical of formula $(CH_2)_n NR^{12}R^{13}$ wherein n is an integer from two to six, and $R^{12}$ and $R^{13}$ each is hydrogen or lower alkyl, or a radical of formula $CO(CH_2)_{n-1}NR^{12}R^{13}$ wherein n, $R^{12}$ and $R^{13}$ are as defined herein, and $R^{17}$ is hydrogen, or $R^{16}$ and $R^{17}$ together form an imine.

A more preferred group of compounds of formula Ib are those in which $R^3$ and $R^4$ are hydrogen; $R^{14}$ and $R^{15}$ each is hydrogen or lower alkyl; $R^{16}$ is hydrogen or a radical of formula $CO(CH_2)_{n-1}NR^{12}R^{13}$ wherein n is an integer from two to six, and $R^{12}$ and $R^{13}$ each is lower alkyl; and $R^{17}$ is hydrogen, or $R^{16}$ and $R^{17}$ together form an imine.

The therapeutically acceptable acid addition salts of the compounds of formula I are also included within the scope of this invention.

This invention involves a pharmaceutical composition comprising a compound of formula I, or a therapeutically acceptable addition salt thereof, and a pharmaceutically acceptable carrier.

The compounds of this invention can be used to treat hypertension in a hypertensive mammal by administering to the mammal an effective antihypertensive amount of a compound of formula I or a therapeutically acceptable addition salt thereof.

DETAILED DESCRIPTION OF THE INVENTION

The term "lower alkyl" as used herein means straight chain alkyl radicals containing from one to six carbon atoms and branched chain alkyl radicals containing three or four carbon atoms and includes methyl, ethyl, propyl, isopropyl, butyl, isobutyl, pentyl, hexyl and the like.

The term "lower alkoxy" as used herein means straight chain alkoxy radicals containing from one to six carbon atoms and branched chain alkoxy radicals containing three or four carbon atoms and includes methoxy, ethoxy, isopropoxy, butoxy, hexanoxy and the like.

The term "lower alkanoyl" as used herein means straight chain alkanoyl radicals containing from two to six carbon atoms and a branched chain alkanoyl radical containing four carbon atoms and includes acetyl, propionyl, isobutyryl, hexanoyl and the like.

The term "lower alkanol" as used herein means both straight and branched chain alkanols containing from one to four carbon atoms and includes methanol, ethanol, isopropanol, butanol and the like.

The term "halo" as used herein means halogens and includes fluorine, chlorine, bromine and iodine, unless stated otherwise.

The term "organic proton acceptor" as used herein means the organic bases, or amines for instance, triethylamine, pyridine, N-ethylmorpholine, 1,5-diazabicyclo[3.4.0]nonene-5 and the like.

The term "complex metal hydride" as used herein means the metal hydrides, including lithium aluminum hydride, lithium aluminum hydride-aluminum chloride, aluminum hydride-aluminum chloride, borane, borane-methyl sulfide, sodium borohydride-aluminum chloride, diisobutylaluminum hydride and the like.

The basic compounds of formula I are capable of forming acid addition salts with therapeutically acceptable acids. The acid addition salts are prepared by reacting the base form of the appropriate compound of formula I with one or more equivalents, preferably with an excess, of the appropriate acid in an organic solvent, for example, diethyl ether or an ethanol-diethyl ether mixture. These salts, when administered to a mammal, possess the same pharmacologic activities as the corresponding bases. For many purposes it is preferable to administer the salts rather than the base compounds. Examples of suitable acids to form these salts include: the common mineral acids, e.g., hydrohalic, sulfuric or phosphoric acids; the organic acids, e.g., formic acetic, maleic, malic, citric, or tartaric acid; and acids which are sparingly soluble in body fluids and which impart slow-release properties to their respective salts, e.g., pamoic acid, tannic acid or carboxymethyl cellulose. The addition salts thus obtained are the functional equivalent of the parent base compound in respect to their therapeutic use. Hence, these addition salts are included within the scope of this invention and are limited only by the requirement that the acids employed in forming the salts be therapeutically acceptable.

Also included in this invention are the stereochemical isomers of the compounds of formula I. Such stereochemical isomers are obtained in substantially pure form by classical separation techniques and by sterically controlled synthesis and have arbitrarily been named as isomers A and B, respectively.

Individual optical enantiomers, which can be separated by fractional crystallization of the diastereomeric salts thereof, for instance, salts with d- or l-tartaric acid or D-(+)-α-bromocamphor sulfonic acid, are also included.

The antihypertensive effect of the compounds of formula I or therapeutically acceptable acid addition salts thereof is demonstrated in standard pharmacological tests, for example, in tests conducted in the spontaneously hypertensive rat (SHR) such as described by I. Varva, et al., Can. J. Physiol. Pharmacol., 51, 727 (1973). More specifically exemplified, the compounds of formula I are shown to be effective antihypertensive agents by using the testing method described in the latter publication. The latter test method is modified so that the test compound is administered to the rat by gastric gavage and the systolic blood pressure is measured by the tail-cuff method before administration of the compound and 1.0 to 4 hours thereafter. Using this method, the following representative compounds of formula I are effective for reducing the systolic blood pressure (BP) in the spontaneously hypertensive rat (the amount of test compound and its reduction in BP are indicated in the parentheses); 1,2,3,4,6,10b-hexahydropyrazino[2,1-a]isoindole (at a dose of 10 mg/kg of body weight causes a 15% reduction in BP at 4 hours, described in Example 7), 9-methoxy-1,2,3,4,6,10-b-hexahydropyrazino[2,1-a]isoindole (at a dose of 10 mg/kg of body causes a 13 to 15% reduction in BP at 4 hours, described in Example 7), 8-methoxy-1,2,3,4,6,10b-hexahydropyrazino[2,1-a]isoindole (at a dose of 1 mg/kg of body weight causes a 18% percent reduction in BP at 1.5 hours, described in Example 7), 8-bromo-1,2,3,4,6,10b-hexahydropyrazino[2,1-a]isoindole (at a dose of 1.0 mg/kg of body weight causes a 10% reduction in BP at 1.5 hours, described in Example 7), 3,3-dimethyl-1,2,3,4,6,10b-hexahydropyrazino[2,1-a]isoindole (at a dose of 25 mg/kg of body weight causes a 21% reduction in BP at 4 hours, described in Example 7), 3-methyl-1,2,3,4,6,10b-hexahydropyrazino[2,1-a]isoindole (at a dose of 25 mg/kg of body weight causes a 10% reduction in BP at 4 hours, described in Example 7), 8-hydroxy-1,2,3,4,6,10b-hexahydropyrazino[2,1-a]isoindole (at a dose of 25 mg/kg of body weight causes a 8 to 15% reduction in BP at 4 hours, described in Example 7), 2-phenylmethyl-1,2,3,4,6,10b-hexahydropyrazino[2,1-a]isoindole (at a dose of 50 mg/kg of body weight causes a 20% reduction in BP at 1.5 hours, described in Example 7), 1,2,3,4,6,10b-hexahydropyrazino[2,1-a]isoindol-6-one (at a dose of 5 mg/kg of body weight causes a 16% reduction in BP at 1.5 hours, described in Example 8), 3-methyl-1,2,3,4,6,10b-hexahydropyrazino[2,1-a]isoindol-6-one (at a dose of 10 mg/kg of body weight causes a 19% reduction in BP at 4 hours, described in Example 8), 3,4-dimethyl-1,2,3,4,6,10b-hexahydropyrazino[2,1-a]isoindol-6-one, isomer A (at a dose of 25 mg/kg of body weight causes a 11% reduction in mean BP over 1.5 to 4 hours, described in Example 8), 3,4-dimethyl-1,2,3,4,6,10b-hexahydropyrazino[2,1-a]isoindol-6-one, isomer B (at a dose of 25 mg/kg causes a 20% reduction in mean BP at 3 hours, described in Example 8), 1,2,3,4,6,10b-hexahydro-2-methylpyrazino[2,1-a]isoindole (at a dose of 10 mg/kg of body weight causes at least a 15% reduction in BP at 1.0 to 4 hours, described in Example 10), 10b-phenylmethyl-1,2,3,4,6,10b-hexahydropyrazino[2,1-a]isoindole (at a dose of 10 mg/kg of body weight causes at 16% reduction in BP at 4 hours, described in Example 11), 2-(4-nitrobenzoyl)-1,2,3,4,6,10b-hexahydropyrazino[2,1-a]isoindol-6-one (at a dose of 25 mg/kg of body weight causes a 20% reduction in BP at 1.0 hours, described in Example 12), 2-methyl-1,2,3,4,6,10b-hexahydropyrazino[2,1-a]isoindole-6-one (at a dose of 10 mg/kg of body weight causes a 8 to 15% reduction in BP at 1.0 to 4 hours, described in Example 13), 2-ethyl-1,2,3,4,6,10b-hexahydropyrazino[2,1-a]isoindol-6-one (at a dose of 25 mg/kg of body weight causes a 16% reduction in mean BP at 1.0 to 4 hours, described in Example 14), 2-(N,N-dimethylaminoacetyl)-1,2,3,4,6,10b-hexahydropyrazino[2,1-a]isoindol-6-one (at a dose of 25 mg/kg of body weight causes a 9% reduction in BP at 1.5 hours, described in Example 15), N,N-dimethyl-1,2,3,4,6,10b-hexahydropyrazino[2,1-a]isoindol-2-propanamine (at a dose of 25 mg/kg of body weight causes a 17% reduction in BP at 4 hours, described in Example 16), 2-ethyl-1,2,3,4,6,10b-hexahydropyrazino[2,1-a]isoindole (at a dose of 25 mg/kg of body weight causes a 20 to 24% reduction in BP at 4 hours, described in Example 17), 10b-methyl-1,2,3,6,10b-hexahydropyrazino[2,1-a]isoindol-6-ol (at a dose of 25 mg/kg of body weight causes a 10% reduction in BP at 4 hours, described in Example 18), 1,2,3,4,6,10b-hexahydro-6-hydroxymethyl-2-phenylmethylpyrazino[2,-a]isoindole (at a dose of 25 mg/kg of body weight cause a 18% reduction in BP at 4 hours, described in Example 259, 1-methyl-1,2,3,6,10b-hexahydropyrazino[2,1-a]isoindol-6-one, isomer A (at a dose of 5 mg/kg of body weight causes a 14% reduction in BP at 4 hours, described in Example 33), 1-methyl-1,2,3,4,6,10b-hexahydropyrazino[2,1-a]isoindol-6-one, isomer B (at a dose of 5 mg/kg of body weight causes a 14% reduction in BP at 4 hours, described in Example 33), 1-ethyl-1,2,3,4,6,10b-hexahydropyrazino[2,1-a]isoindol-6-one, isomer B (at a dose of 25 mg/kg of body weight causes a 18% reduction in mean BP at 1.0 to 4.0 hours, described in Example 34), 1-methyl-1,2,3,4,6,10b-hexahydropyrazino[2,1-a]isoindole, isomer A (at a dose of 25 mg/kg of body weight causes a 14% reduction in BP at 4 hours, described in Example 35), 1-methyl-1,2,3,4,6,10b-hexahydropyrazino[2,1-a]isoindole, isomer B (at a dose of 25 mg/kg of body weight causes a 23% reduction in mean BP at 0.5 to 4 hours, described in Example 35), 1,10b-dihydro-2,2-dimethylpyrimido[6,1-a]isoindol-6(2H)-one (at a dose of 25 mg/kg of body weight causes a 8 to 14% reduction in BP at 1 to 4 hours, described in Example 37), 1,3,4,10b-tetrahydro-2,2-dimethylpyrimido[6,1-a]isoindol-6(2H)-one (at a dose of 50 mg/kg of body weight causes a 8 to 11% reduction in BP at 1 to 4 hours, described in Example 38) and 1,3,4,10b-tetrahydropyrimido[6,1-a]isoindol-6(2H)-one (at a dose of 25 mg/kg of body weight causes a 8 to 14% reduction in BP at 1 to 4 hours, described in Example 40).

The compounds of formula I of this invention are used alone or in combination with pharmacologically acceptable carriers, the proportion of which is determined by the solubility and chemical nature of the compound, chosen route of administration and standard biological practice. For example, they are administered orally in solid form i.e. capsule or tablet. They can also be administered orally in the form of suspensions or solutions or they may be injected parenterally. For parenteral administration they can be used in the form of a sterile solution containing other solutes, for example, enough saline or glucose to make the solution isotonic.

The tablet compositions contain the active ingredient in admixture with non-toxic pharmaceutical excipients known to be suitable in the manufacture of tablets. Suitable pharmaceutical excipients are, for example, starch, milk sugar, certain types of clay and so forth. The tablets can be uncoated or they can be coated by known techniques so as to delay disintegration and absorption in the gastrointestinal tract and thereby provide a sustained action over a longer period.

The aqueous suspensions of the compounds of formula I contain the active ingredient in admixture with one or more non-toxic pharmaceutical excipients known to be suitable in the manufacture of aqueous suspensions. Suitable excipients are, for example, methylcellulose, sodiumm alginate, gum acacia, lecithin and so forth. The aqueous suspensions can also contain one or more preservatives, one or more coloring agents, one or more flavouring agents and one or more sweetening agents.

Non-aqueous suspensions can be formulated by suspending the active ingredient in a vegetable oil, for example, arachis oil, olive oil, sesame oil, or coconut oil, or in a mineral oil, for example liquid paraffin, and the suspension may contain a thickening agent, for example beeswax, hard paraffin or cetyl alcohol. These compositions can also contain a sweetening agent, flavouring agent and antioxidant.

The dosage of the compounds of formula I as antihypertensive agents will vary with the form of administration and the particular compound chosen. Furthermore, it will vary with the particular host as well as the age and condition of the host under treatment. Generally, treatment is initiated with small dosages substantially less than the optimum dose of the compound. Thereafter, the dosage is increased by small increments until the optimum effect under circumstances is reached. In general, the compounds of this invention are most desirably administered at a concentration level that will generally afford effective results without causing any harmful or deleterious side effects. The effective antihypertensive amount of the compounds usually ranges from about 0.1 mg to about 250 mg per kilogram body weight per day, although as aforementioned variations will occur. However a dosage level that is in the range of from about 1.0 mg to about 100 mg per kilogram body weight per day is employed most desirably in order to achieve effective results.

The compound of formula I, or a therapeutically acceptable salt thereof, also can be used to produce beneficial effects in the treatment of hypertension, peripheral and cerebral vascular diseases and related disorders when combined with a therapeutically effective amount of a diuretic and/or antihypertensive agent commonly used in antihypertensive therapy. Such antihypertensive therapeutic agents include, for example, the thiazide diuretics for instance, chlorothiazide or hydrochlorothiazide; mineralocorticoid antagonizing diuretic agents, e.g., spironolactone; and other diuretics such as triamterene and furosemide. Examples of still other suitable antihypertensive agents are prazosin, hydralazine and centrally active antihypertensive agents such as methyldopa, clonidine, and reserpine; as well as the β-adrenergic blocking agents, for instance, propanolol. In this instance, the compound of formula I, or its therapeutically acceptable acid addition salt can be administered sequentially or simultaneously with the antihypertensive and/or diuretic agent. Preferred antihypertensive therapeutic agents are the antihypertensive agents such as the thiazides, mineralocorticoid antagonizing diuretic agents and the β-adrenergic blocking agents. A combination of the foregoing antihypertensive and/or diuretic agents, e.g. propranolol and hydrochlorothiazide, can be substituted for a single agent. Suitable methods of administration, compositions and dosages of the above described diuretic and/or antihypertensive agents are well known in the art; for instance, "Physicians' Desk Reference", 32 ed., Medical Economics Co., Oradell, N.J., U.S.A., 1978. For example, the agent propranolol is administered daily to humans in a range of 80 to 640 mg, usually in the form of unit doses of 10, 20, 40 or 80 mg. When used in combination, the compound of formula I, or its therapeutically acceptable salt is administered as described previously.

In addition to having antihypertensive activity, some of the compounds of formula I or a therapeutically acceptable acid addition salt thereof possess valuable anthelmintic activity. The compounds can be tested for their anthelmintic properties by the anthelmintic test system described by H. J. Howes, Jr. and J. E. Lynch, Journal of Parasitology, 53, 1085 (1967).

In a modification of this test system, five mice per group are used in the test. Each mouse is fasted for 24 hours and doubly infected via gavage with 40 eggs of *Hymenolepis nana and* 1500 larvae of *Nematospiroides dubius* suspended in 0.5 ml of 0.1 % bacto agar. After 14 days, the test compound is mixed at a concentration of 0.2% in soft diet and each mouse is allowed to eat 30 grams of this diet. The control group of infected mice does not receive the test compound. Four days later, the mice are sacrificed and the *H. nana* tapes are recovered from the lower intestines. Efficacy of the test compound is determined by the percent removal of tapes when compared to the infected control. In the above test the following compounds of formula I are effective against *H. nana* tapes (the percent reduction of the tapes is indicated in the parenthesis): 2-cyclohexylcarbonyl-1,2,3,4,6,10b-hexahydropyrazino[2,1-a]isoindol-6-one (91%, described in Example 12) and 2-(N,N-dimethylaminoacetyl)-1,2,3,4,6,10b-hexahydropyrazino[2,1-a]isoindol-6-one (10%, described in Example 15).

When used as anthelmintic agents, the compounds of formula I can be administered to the mammal in feed at levels of about 0.01 to 0.5% by weight, in drinking water at levels of about 0.02 to 0.6% by weight as well as by oral or parenteral routes. Generally, dosages of about 0.1 to 5.0 mg/kg of body weight daily will generally suffice to effectively clear the animal of the infectious organisms. Anthelmintic compositions comprising an effective amount of a compound either alone or in combination with other active therapeutic ingredients in admixture with suitable carriers can be readily prepared according to conventional pharmaceutical and veterinary techniques for the usual routes of administration.

Process

The process for the preparation of the compounds of formula I is illustrated by the following description of the different embodiments of this invention.

(a) Preparation of the Compounds of Formula Ia

Reaction scheme I illustrates an embodiment for the preparation of the compounds of formula Ia in which $R^1$ and $R^6$ are hydrogen; $R^2$ is hydrogen or hydroxy; or $R^1$ and $R^2$ together form a ketone; and $R^3$, $R^4$, $R^5$, $R^7$, $R^8$, $R^9$, $R^{10}$ and $R^{11}$ are as defined herein.

Reaction Scheme 1

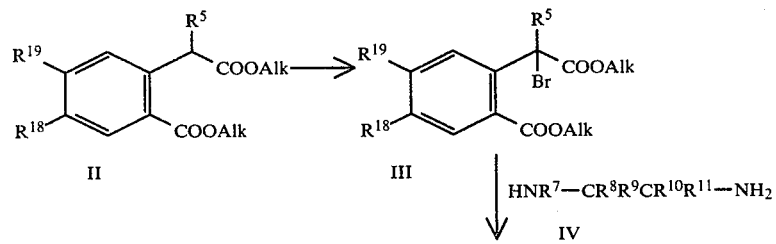

Reaction Scheme 1

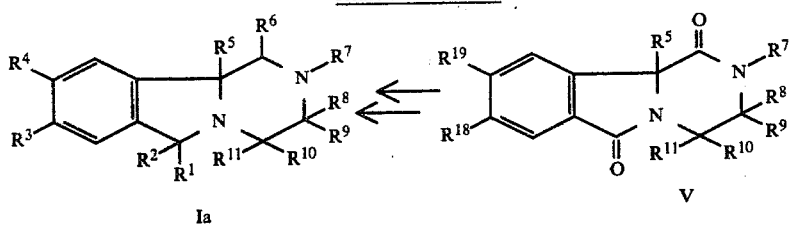

The starting materials of formula II in which $R^{18}$ and $R^{19}$ each is hydrogen, lower alkoxy, lower alkyl, trifluoromethyl, halo or methoxymethyleneoxy or $R^{18}$ and $R^{19}$ together form a $OCH_2O$ chain, $R^5$ is as defined herein and Alk is lower alkyl are obtained by esterifying the appropriate 2-carboxyphenylacetic acid. This esterification is preferably achieved by heating a solution of the appropriate 2-carboxyphenylacetic acid in an anhydrous lower alkanol, preferably methanol or ethanol, in the presence of hydrogen chloride at 60° to 80° C. for 10 to 20 hours.

The 2-carboxyphenylacetic acids are either known and commercially available or can be prepared by using the appropriate reagents and following a known procedure, for example, see the reports by W. H. Perkin and R. Robinson, J. Chem. Soc., 1073(1907), D. E. Ames and T. F. Grey, J. Chem. Soc., 3518 (1955) and H. E. Ungnade et al., J. Org. Chem., 10, 533 (1945).

Bromination of the compound of formula II affords the bromo derivative of formula III in which $R^5$, $R^{18}$, $R^{19}$ and Alk are as defined herein. The preferred method of bromination is the reaction of the compound of formula II with 1.1 molar equivalents of N-bromosuccinimide in carbon tetrachloride at 70° to 80° C. for one to four hours while irradiating with a 500 watt photospot lamp.

Condensation of the compound of formula III with an ethylenediamine of formula IV in which $R^7$ is hydrogen, lower alkyl or phenylmethyl and $R^8$, $R^9$, $R^{10}$ and $R^{11}$ are as defined herein in the presence of an organic proton acceptor gives the corresponding tricyclic compound of formula V in which $R^5$, $R^8$, $R^9$, $R^{10}$, $R^{11}$, $R^{18}$ and $R^{19}$ are as defined herein and $R^7$ is hydrogen, lower alkyl or phenylmethyl. Generally about 1.1 to 3.0 molar equivalents of the ethylenediamine of formula IV and about 1.1 to 2.0 molar equivalents of the organic proton acceptor, preferably triethylamine or N-methylmorpholine, are required. An inert organic solvent is usually employed for this condensation. Suitable inert organic solvents can be selected from the diethyl ethers or cyclic ethers, preferably tetrahydrofuran or dioxane. The reaction mixture is maintained at 50° to 80° C. for one to five hours in order to obtain the compound of formula V.

The compound of formula V, obtain as described above, can be further transformed to obtain other compounds of formula V. For example, the compound of formula V in which $R^5$ is hydrogen can be benzylated, preferably by reacting the latter compound of formula V with about an equal weight of 10% palladium on carbon in toluene at reflux temperature for 15 to 30 hours, to obtain the corresponding compound of formula V in which $R^5$ is phenylmethyl.

Subsequently, the compounds of formula V are converted to the corresponding compounds of formula Ia in which $R^1$ and $R^6$ are hydrogen; $R^2$ is hydrogen or hydroxy; or $R^1$ and $R^2$ together form a ketone; and $R^5$, $R^7$, $R^8$, $R^9$, $R^{10}$ and $R^{11}$ are as defined herein by the step(s), in optional order, of reduction and, when desired, of alkylation, amidation or acylation.

Reduction of the compound of formula V can be controlled to give the corresponding compound of formula Ia in which $R^1$ and $R^2$ together form a ketone or $R^1$ and $R^2$ are hydrogen or $R^1$ is hydrogen and $R^2$ is hydroxy. Suitable reducing agents can be selected from the complex metal hydrides; lithium aluminum hydride and borane are the preferred reducing agents.

Selective reduction of the compound of formula V under mild conditions with borane in an inert organic solvent gives the corresponding compound of formula I in which $R^1$ and $R^2$ together form a ketone; $R^3$, $R^4$, $R^5$, $R^8$, $R^9$, $R^{10}$ and $R^{11}$ are as defined herein; $R^6$ is hydrogen, and $R^7$ is hydrogen, lower alkyl or phenylmethyl. For this controlled selective reduction about two to four molar equivalents of borane are required and the reduction is conducted at −15° to 30° C., preferably 15° to 25° C., for one to six hours, preferably three to five hours. Suitable inert organic solvents can be selected from a dialkyl ether or cyclic ether, preferably diethyl ether, tetrahydrofuran or dioxane.

Reduction of the compound of formula V under more vigorous conditions with 5 to 20 molar equivalents of borane in an inert organic solvent gives the corresponding compound of formula I in which $R^1$, $R^2$ and $R^6$ are hydrogen; $R^3$, $R^4$, $R^5$, $R^8$, $R^9$, $R^{10}$ and $R^{11}$ are as defined herein, and $R^7$ is hydrogen, lower alkyl or phenylmethyl. The latter reduction is usually conducted at 60° to 80° C. for 15 to 30 hours. Suitable inert organic solvents are the same as defined above for the selective reduction; tetrahydrofuran or dioxane is the preferred solvent for this reduction.

The use of lithium aluminum hydride as the reducing agent for the reduction of the compound of formula V gives the corresponding compound of formula Ia in which $R^1$ and $R^6$ are hydrogen; $R^2$ is hydroxy; $R^3$, $R^4$, $R^5$, $R^8$, $R^9$, $R^{10}$ and $R^{11}$ are as defined herein, and $R^7$ is hydrogen, lower alkyl or phenylmethyl. In this case, four to eight molar equivalents of lithium aluminum hydride is used. An inert organic solvent, selected from those described above for use with borane, preferably tetrahydrofuran or dioxane, are suitable for this reduction. It may be necessary to heat the reaction mixture of the compound of formula V and lithium aluminum hydride in the inert organic solvent at 50° to 80° C. for 10 to 30 hours.

The above reductions of the compounds of formula V usually require acidification of the reduction mixture in order to destroy any excess of the reducing agent. This acidic destruction of the reducing agent is usually sufficiently acidic to hydrolyze the protecting group on the phenol (i.e. $R^{18}$ and/or $R^{19}$ is methoxymethyleneoxy to the corresponding alcohol (i.e. $R^3$ and/or $R^4$ is hydroxy). If however the methoxymethyleneoxy group is not hydrolyzed during the acidic work-up of the reduction, the methoxymethyleneoxy group can be conveniently hydrolyzed under acidic conditions in a separate step. Suitable acidic conditions can be selected from 50 to 90% acetic acid at 90° to 100° C. for 20 to 30 hours or 5 to 20% hydrochloric or hydrobromic acid at 25° to 90° C. for 5 to 30 hours.

If desired, the compounds of formula Ia in which $R^7$ is hydrogen, prepared as described above, can be further transformed to obtain other compounds of formula Ia. Since these transformations involve the substitution of the secondary nitrogen in the above compounds of formula Ia (i.e., $R^7$ is hydrogen), any alcohol groups (i.e., $R^2$, $R^3$ and/or $R^4$ is hydroxy), if present, should be protected in order to avoid substitution of these alcohol groups. The alcohol is conveniently and preferably protected as the acetate. Usually, this acetylation is achieved by reacting the alcoholic compound of formula Ia with a molar excess of acetic anhydride at 100° to 139° C. for one to ten hours in the presence of an acid catalyst, preferably p-toluenesulfonic or hydrochloric acid. The acetate group is easily removed at a later step by reduction with a complex metal hydride in the same manner as described above or by alkaline hydrolysis with an aqueous and/or alcoholic solution of sodium or potassium hydroxide.

One useful transformation is to alkylate or benzylate the secondary nitrogen in the above described compounds of formula Ia in which $R^7$ is hydrogen to obtain the corresponding compound of formula Ia in which $R^7$ is lower alkyl or phenylmethyl. Alkylation or benzylation is readily obtained by reacting the above described compound of formula Ia with about a molar equivalent of a lower alkyl or phenylmethyl chloride, bromide or iodide and about 1.0 to 1.5 molar equivalents of sodium hydride in an inert organic solvent, preferably benzene or toluene, at 40° to 60° C. for 15 to 30 hours.

Another useful method of introducing a methyl group is to react the above described compound of formula Ia with about four to six molar equivalents of 90% formic acid and about two to four molar equivalents of 37% formaldehyde at 90° to 105° C. for five to ten hours to obtain the corresponding compound of formula Ia in which $R^7$ is methyl.

Still another useful method of introducing a methyl group is the reaction of compound of formula Ia in which $R^7$ is hydrogen with one to two molar equivalents of ethyl chloroformate and an organic proton acceptor, preferably triethylamine, in benzene or toluene at 0° to 20° C. for 15 minutes to five hours. The resulting formate is then reduced with four to seven molar equivalents of lithium aluminum hydride in tetrahydrofuran at 10° to 20° C. for 15 minutes to three hours to obtain the corresponding compound of formula Ia in which $R^7$ is methyl.

Another transformation is the acylation of the secondary nitrogen in the above described compounds of formula Ia in which $R^7$ is hydrogen to obtain the corresponding compounds of formula Ia in which $R^7$ is lower alkanoyl, cyclohexylcarbonyl, benzoyl, or 4-nitrobenzoyl. For this acylation, substantially equimolar equivalent amounts of the compound of formula Ia in which $R^7$ is hydrogen, an organic proton acceptor, preferably triethylamine, and a chloride, bromide or iodide of a lower alkanoyl, cyclohexylcarbonyl, benzoyl or 4-nitrobenzoyl in an inert organic solvent, preferably benzene, are reacted at 0° to 15° C. for two to 30 minutes.

The latter acylation is also applicable to the compounds of formula V. For example, the secondary nitrogen in the compound of formula V is acylated, in the same manner as described above, to obtain the corresponding compound of formula V in which $R^7$ is lower alkanoyl, cyclohexylcarbonyl, benzoyl or 4-nitrobenzoyl.

Reduction of the latter compounds of formula V with borane at $-15°$ to 30° C., in the same manner as described above affords the corresponding compound of formula Ia in which $R^1$ and $R^2$ together form a ketone; $R^3$, $R^4$, $R^5$, $R^8$, $R^9$, $R^{10}$ and $R^{11}$ are as defined herein; $R^6$ is hydrogen; and $R^7$ is lower alkanoyl, cyclohexylcarbonyl, benzoyl or 4-nitrobenzoyl.

If desired, the above described compound of formula Ia in which $R^7$ is lower alkanoyl can be reduced with lithium aluminum hydride by reacting the latter compound of formula Ia with four to six molar equivalents of lithium aluminum hydride in tetrahydrofuran at 10° to 30° C. for 15 to 30 hours to obtain the corresponding compound of formula Ia in which $R^7$ is lower alkyl containing two to six carbon atoms.

Reduction of the above described compound of formula Ia in which $R^7$ is 4-nitrobenzoyl with hydrogen in the presence of noble metal hydrogenation catalyst, preferably 5% palladium on carbon, in a lower alkanol, preferably ethanol, gives the corresponding compound of formula Ia in which $R^1$ and $R^6$ are hydrogen; $R^2$ is hydrogen or hydroxy or $R^1$ and $R^2$ together form a ketone; $R^3$, $R^4$, $R^5$, $R^8$, $R^9$, $R^{10}$ and $R^{11}$ are as defined herein; $R^6$ is hydrogen; and $R^7$ is 4-aminobenzoyl.

Another transformation of the compound of formula Ia in which $R^7$ is hydrogen is the reaction of the latter compound with about equimolar amounts of cyanogen bromide and triethylamine in tetrahydrofuran at 0° to 30° C. for 30 to 60 minutes to obtain the corresponding compound of formula Ia in which $R^7$ is aminocarbonyl.

Another transformation of the compound of formula Ia in which $R^7$ is hydrogen is the reaction of the latter compound with about equimolar equivalents of sodium hydride and about 1.1 molar equivalents of ethyl bromoacetate in benzene at 60° to 80° C. for two to five hours to obtain the corresponding ester. Hydrolysis of the latter ester with about an equimolar amount of sodium or potassium hydroxide in an aqueous ethanolic or methanolic solution at 20° to 30° C. for two to five hours and acidication, preferably with dilute hydrochloric acid, of the latter solution gives the corresponding compound of formula Ia in which $R^7$ is carboxymethyl.

Still another transformation of the compound of formula Ia in which $R^7$ is hydrogen is the reaction of the latter compound with about 1.1 molar equivalents of a compound of formula $X-CO-(CH_2)_{n-1}-X^1$ wherein n is an integer from two to six and X and $X^1$ each is chloro, bromo or iodo in the presence of an organic proton acceptor, preferably triethylamine, in an inert organic solvent, preferably benzene, at 20° to 30° C. for 15 minutes to two hours to afford the corresponding intermediate having the radical $-CO-(CH_2)_{n-1}-X^1$ in which $X^1$ and n are as defined herein. Subsequently, the latter intermediate is reacted with about 5 to 15 molar equivalents of an amine of formula $HNR^{12}R^{13}$ wherein $R^{12}$ and $R^{13}$ each is hydrogen or lower alkyl in an inert organic solvent, preferably tetrahydrofuran, at 20° to 60° C. for 10 to 30 hours to obtain the corresponding compound of formula Ia in which $R^7$ is a radical of formula $CO(CH_2)_{n-1}NR^{12}R^{13}$ wherein n, $R^{12}$ and $R^{13}$ are as defined herein.

The latter compound of formula Ia can be reduced with a complex metal hydride, preferably with about five to ten molar equivalents of borane in an inert organic solvent, preferably tetrahydrofuran or dioxane, at 60° to 70° C. for 15 to 30 hours, to obtain the corresponding compound of formula Ia in which $R^7$ is a radical of formula $(CH_2)_nNR^{12}R^{13}$ wherein n, $R^{12}$ and $R^{13}$ are as defined herein.

Reaction scheme 2 illustrates the preferred method for the preparation of the compounds of formula Ia in which $R^1$ and $R^6$ are hydrogen; $R^2$ is hydroxymethyl; and $R^3$, $R^4$, $R^5$, $R^7$, $R^8$, $R^9$, $R^{10}$ and $R^{11}$ are as defined herein.

$R^{11}$, $R^{18}$, $R^{19}$ and Alk are as defined herein and $R^7$ is phenylmethyl.

Treatment of the compound of formula VIII in which $R^{20}$ is 1,1-dimethylethoxycarbonyl with a strong acid, for example, trifluoroacetic acid, sulfuric acid or hydrochloric acid, preferably in a solution of 10 to 30% hydrochloric acid and ethyl acetate at 50° to 70° C. for one to three hours, removes the 1,1-dimethylethoxycarbonyl group and the resulting primary amine undergoes a spontaneous cyclization to the corresponding compound of formula IX in which $R^5$, $R^8$, $R^9$, $R^{10}$, $R^{11}$, $R^{18}$, $R^{19}$ and Alk are as defined herein and $R^7$ is hydrogen.

In the above cyclizations, the compound of formula IX is usually formed as a mixture of diastereomers. The diastereomers can be separated, for example, by chromatography, crystallization and the like, to obtain the

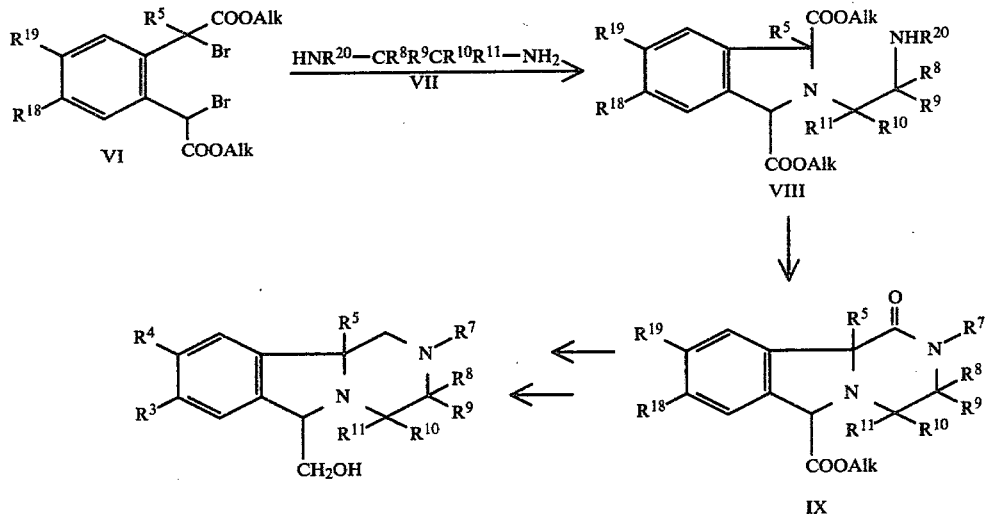

Reaction Scheme 2

Ia in which $R^1$ and $R^6$ are hydrogen,
$R^2$ is hydroxymethyl and $R^3,R^4,R^5,R^7$,
$R^8,R^9,R^{10}$ and $R^{11}$ are as defined herein.

The starting materials of formula VI are either known, for example, α,-α'-dibormo-o-benzenediacetic acid dimethyl ester is described by G. Cignarella and A. Vigevani, Gass. Chim. Ital., 98, 1474 (1968), or can be prepared by using the method described in the latter reference.

Condensation of the compound of formula VI in which $R^5$, $R^{18}$, $R^{19}$ and Alk are as defined herein with about 1.1 to 3 molar equivalents of an ethylenediamine of formula VII in which $R^{20}$ is phenylmethyl or 1,1-dimethylethoxycarbonyl and $R^8$, $R^9$, $R^{10}$ and $R^{11}$ are as defined herein in the presence of an organic proton acceptor, preferably about 2.5 to 5 molar equivalents of triethylamine or N-ethylmorpholine, at 50° to 100° C. for three to ten hours gives the corresponding compound of formula VIII in which $R^5$, $R^8$, $R^9$, $R^{10}$, $R^{11}$, $R^{18}$, $R^{19}$, $R^{20}$ and Alk are as defined herein. Suitable organic solvents for this condensation can be selected from benzenes, alkyl-benzenes, preferably toluene or xylene, and cyclic ethers; benzene and toluene are the preferred solvents. Usually, the latter compound of formula VIII in which $R^{20}$ is phenylmethyl cannot be isolated from the reaction mixture since this compound undergoes a spontaneous cyclization to the corresponding compound of formula IX in which $R^5$, $R^8$, $R^9$, $R^{10}$, separate diastereomers, arbitarily called isomers A and B.

The compound of formula IX in which $R^7$ is hydrogen can be alkylated with a lower alkyl chloride, bromide or iodide, in the same manner as described above, to obtain the corresponding compound of formula IX in which $R^7$ is lower alkyl and $R^5$, $R^8$, $R^9$, $R^{10}$, $R^{11}$, $R^{18}$, $R^{19}$ and Alk are as defined herein.

Reduction of the above described compound of formula IX with a complex metal hydride, preferably borane at 60° to 80° C. for 10 to 30 hours in an inert organic solvent, preferably tetrahydrofuran, gives the corresponding compound of formula Ia in which $R^1$ and $R^6$ are hydrogen; $R^2$ is hydroxymethyl; $R^3$, $R^4$, $R^5$, $R^8$, $R^9$, $R^{10}$ and $R^{11}$ are as defined herein; and $R^7$ is hydrogen, lower alkyl or phenylmethyl. If required, the phenol protecting group (i.e. $R^{18}$ and/or $R^{19}$ is methoxymethyleneoxy) is hydrolyzed with an acid, in the same manner as described above, to obtain the corresponding phenolic compound of formula Ia (i.e. $R^3$ and/or $R^4$ is hydroxy).

If desired, the ester group in the compound of formula IX is selectively reduced with lithium borohydride in tetrahydrofuran at 60° to 80° C. for 10 to 30 hours to obtain the corresponding intermediate of formula IX wherein the ester is reduced to hydroxymethyl.

Reduction of the latter intermediate with borane in the same manner as described above affords the corresponding compound of formula Ia in which $R^2$ is hydroxymethyl.

The latter compound of formula Ia in which $R^2$ is hydroxymethyl and $R^7$ is hydrogen can be converted to other compounds of formula Ia. The first step in this conversion is to protect the hydroxy group(s) present, i.e. $R^2$ is hydroxymethyl, $R^3$ and/or $R^4$ is hydroxy. The hydroxy group is preferably protected as the acetate. To introduce the acetate protection, the compound of formula Ia is reacted with about one molar equivalent of acetic anhydride per hydroxy group in the presence of about 0.01 molar equivalent of an acid catalyst, for example, p-toluenesulfonic acid, hydrochloric acid, sulfuric acid or hydrobromic acid to obtain the corresponding acetate protected intermediate.

Alkylation or acylation of the latter acetate protected intermediate, in the same manner as described above, followed by hydrolysis of the acetate, preferably with an aqueous methanolic solution of sodium hydroxide at 0° to 40° C., affords the corresponding compound of formula Ia in which $R^1$ and $R^6$ are hydrogen, $R^2$ is hydroxymethyl, $R^3$, $R^4$, $R^5$, $R^8$, $R^9$, $R^{10}$ and $R^{11}$ are as defined herein and $R^7$ is lower alkyl, lower alkanoyl, cyclohexylcarbonyl, benzoyl or 4-nitrobenzoyl.

Reduction of the latter compound of formula Ia in which $R^7$ is 4-nitrobenzoyl with hydrogen in the presence of a noble metal hyrogenation catalyst, in the same manner as described above, gives the corresponding compound of formula Ia in which $R^7$ is 4-aminobenzoyl.

Reaction of the above noted acetate protected intermediate with ethyl bromoacetate and sodium hydride followed by alkaline hydrolysis, in the same manner as described above, gives the corresponding compound of formula Ia in which $R^1$ and $R^6$ are hydrogen, $R^2$ is hydroxymethyl, $R^3$, $R^4$, $R^5$, $R^8$, $R^9$, $R^{10}$ and $R^{11}$ are as defined herein and $R^7$ is carboxymethyl.

Another transformation of the above noted acetate protected intermediate is the reaction of the latter intermediate with a compound of formula $X—CO—(CH_2)_{n-1}—X^1$ in which n, X and $X^1$ are as defined herein followed by amination with an amine of formula $HNR^{12}R^{13}$ in which $R^{12}$ and $R^{13}$ are as defined herein, in the same manner as described above, to obtain the corresponding amide having the acetate protecting group. Reduction of the latter intermediate with a complex metal hydrid, in the same manner as described above, gives the corresponding compound of formula Ia in which $R^1$ and $R^6$ are hydrogen, $R^2$ is hydroxymethyl, $R^3$, $R^4$, $R^5$, $R^8$, $R^9$, $R^{10}$ and $R^{11}$ are as defined herein and $R^7$ is a radical of formula $(CH_2)_n NR^{12}R^{13}$ wherein n, $R^{12}$ and $R^{13}$ are as defined herein. The above noted amide having the acetate protecting group can be hydrolyzed with an aqueous methanolic solution of sodium hydroxide, in the same manner as described above, to obtain the corresponding compound of formula Ia in which $R^1$ and $R^6$ are hydrogen, $R^2$ is hydroxymethyl, $R^3$, $R^4$, $R^5$, $R^8$, $R^9$, $R^{10}$ and $R^{11}$ are as defined herein and $R^7$ is a radical of formula $CO—(CH_2)_{n-1}—NR^{12}R^{13}$ wherein n, $R^{12}$ and $R^{13}$ are as defined herein.

Reaction of the above noted acetate protected intermediate with cyanogen bromide and triethylamine followed by alkaline hydrolysis, in the same manner as described above, gives the corresponding compound of formula Ia in which $R^1$ and $R^6$ are hydrogen, $R^2$ is hydroxymethyl, $R^3$, $R^4$, $R^5$, $R^8$, $R^9$, $R^{10}$ and $R^{11}$ are as defined herein and $R^7$ is aminocarbonyl.

Reaction scheme 3 illustrates the preferred method for the preparation of the compounds of formula Ia in which $R^1$ and $R^2$ are hydrogen or $R^1$ and $R^2$ together form a ketone; $R^3$, $R^4$, $R^6$, $R^7$, $R^{10}$ and $R^{11}$ are as defined herein; and $R^5$, $R^8$ and $R^9$ are hydrogen.

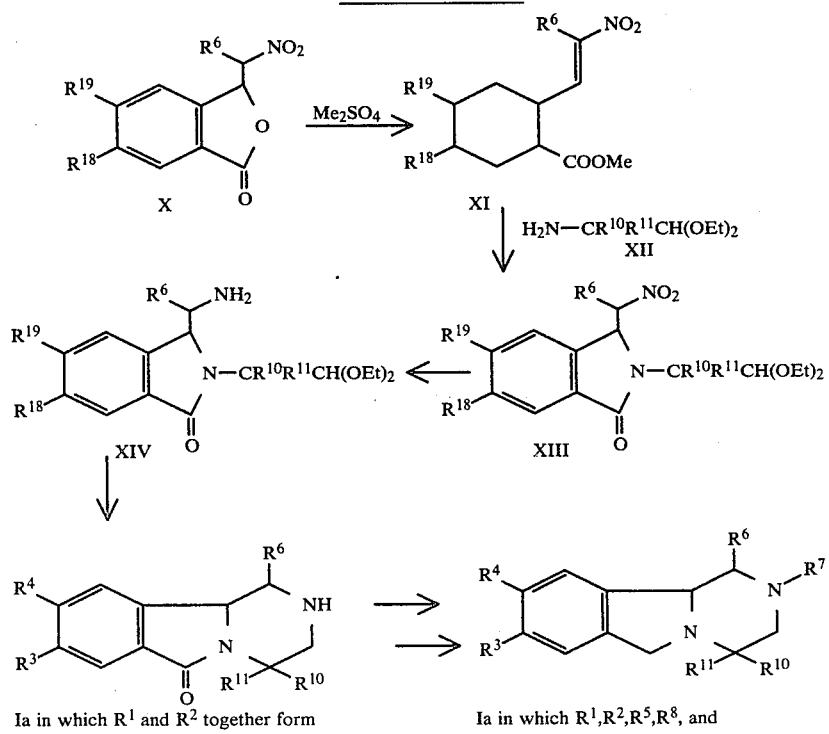

Reaction Scheme 3

| Reaction Scheme 3 -continued | |
|---|---|
| a ketone, $R^3, R^4, R^6, R^{10}$ and $R^{11}$ are as defined herein and $R^5, R^7$ $R^8$ and $R^9$ are hydrogen. | $R^9$ are hydrogen and $R^3, R^4$, $R^6, R^7, R^{10}$ and $R^{11}$ are as defined herein. |

With reference to reaction scheme 3, the starting materials of formula X are either known, for example, 1,3-dihydro-α-nitro-3-oxo-isobenzofuran-1-ethane is described by J. J. Stehle et al., J. Org. Chem., 10, 429 (1945), or can be prepared by using the procedure of the latter publication and the appropriate reactants.

Methylation of the compound of formula X with diazomethane or dimethylsulfate gives the styrene derivatives of formula XI in which $R^6$, $R^{18}$ and $R^{19}$ are as defined herein. The preferred method of methylation involves the use of 1.2 to 1.9 molar equivalents of dimethylsulfate and 1.5 to 3 molar equivalents of potassium carbonate in acetone at 20° to 30° C. for 15 to 30 hours.

The styrene derivatives of formula XI is condensed with 1.1 to 2.0 molar equivalents of an amine of formula XII in the presence of 1.5 to 2.5 molar equivalents of a weak proton acceptor, preferably sodium acetate, to obtain the corresponding isoindole of formula XIII in which $R^6$, $R^{10}$, $R^{11}$, $R^{18}$ and $R^{19}$ are as defined herein. The preferred solvent for this condensation is acetonitrile and the condensation is conducted at 20° to 30° C. for 15 to 30 hours. The compound of formula XIII usually forms as a mixture of two diastereomers which can be separated or the mixture can be further reacted and the diastereomers are separated later.

Reduction of the isoindole of formula XIII in the presence of a noble metal hydrogenation catalyst, preferably 10% palladium on carbon, in a suitable solvent, preferably aqueous acetic acid, under an atmosphere of hydrogen at 30 to 70 psi for 10 to 30 hours gives the corresponding aminoisoindole of formula XIV in which $R^6$, $R^{10}$, $R^{11}$, $R^{18}$ and $R^{19}$ are as defined herein. If the mixture of two diastereomers of formula XIII is used for this reduction, the resulting diastereomeric mixture of formula XIV can be conveniently separated by chromatography to obtain the individual isomers A and B of formula XIV.

A mixture of the compound of formula XIV and a noble metal hydrogenation catalyst, preferably 10% palladium on carbon, in a solution of methanol, ethanol or acetic acid and 1 N to 6 N hydrobromic or hydrochloric acid is stirred under an atmosphere of hydrogen at one to four atmospheres pressure and at 25° to 80° C. for 6 to 50 hours to obtain the corresponding compound of formula Ia in which $R^1$ and $R^2$ together form a ketone, $R^3$, $R^4$, $R^6$, $R^{10}$ and $R^{11}$ are as defined herein and $R^5$, $R^7$, $R^8$ and $R^9$ are hydrogen.

If desired, the compound of formula XIII can be hydrogenated in the presence of hydrobromic or hydrochloric acid, in the same manner as described immediately above, to obtain directly the corresponding compounds of formula Ia without isolating the compound of formula XIV.

In the latter acidic hydrogenations, either the individual isomers A or B, or the diastereomeric mixture of the compound of formula XIII or XIV can be used. When the diastereomeric mixture is used, the resulting diastereomeric mixture of the compound of formula Ia is readily separated by chromatography and/or crystallization to obtain the individual isomers A and B of the corresponding compound of formula Ia.

Furthermore, the above acidic hydrogenation of the compound of formula XIII or XIV is usually sufficiently acidic to hydrolyze the phenol protecting group, i.e. $R^{18}$ and/or $R^{19}$ is methoxymethyleneoxy, so that the corresponding phenolic derivative, i.e. $R^3$ and/or $R^4$ is hydroxy, is obtained.

If desired, the compound of formula Ia, obtained from the latter described hydrogenation, can be converted to other compounds of formula Ia.

The reduction of the compound of formula Ia in which $R^1$ and $R^2$ together form a ketone, $R^3$, $R^4$, $R^6$, $R^{10}$ and $R^{11}$ are as defined herein and $R^5$, $R^7$, $R^8$ and $R^9$ are hydrogen with a complex metal hydride, preferably with borane in tetrahydrofuran at 50° to 70° C. for 15 to 30 hours, gives the corresponding compound of formula Ia in which $R^1$, $R^2$, $R^5$, $R^7$, $R^8$ and $R^9$ are hydrogen and $R^3$, $R^4$, $R^6$, $R^{10}$ and $R^{11}$ are as defined herein.

Alkylation, acylation or benzylation of the compound of formula Ia in which $R^1$, $R^2$, $R^5$, $R^7$, $R^8$ and $R^9$ are hydrogen or $R^1$ and $R^2$ together form a ketone and $R^3$, $R^4$, $R^6$, $R^{10}$ and $R^{11}$ are as defined herein, in the same manner as described above, gives the corresponding compound of formula Ia in which $R^1$, $R^2$, $R^8$ and $R^9$ are hydrogen, or $R^1$ and $R^2$ together form a ketone; $R^3$, $R^4$, $R^6$, $R^{10}$ and $R^{11}$ are as defined herein, and $R^7$ is lower alkyl, lower alkanoyl, cyclohexylcarbonyl, benzoyl, 4-nitrobenzoyl or phenylmethyl.

Reduction of the latter compound of formula Ia in which $R^7$ is 4-nitrobenzoyl, in the same manner as described above, gives the corresponding compound of formula Ia in which $R^7$ is 4-aminobenzoyl.

Reaction of the compound of formula Ia in which $R^1$, $R^2$, $R^7$, $R^8$ and $R^9$ are hydrogen or $R^1$ and $R^2$ together form a ketone and $R^3$, $R^4$, $R^6$, $R^{10}$ and $R^{11}$ are as defined herein with ethyl bromoacetate and sodium hydride followed by alkaline hydrolysis, in the same manner as described above, gives the corresponding compound of formula Ia in which $R^1$, $R^2$, $R^5$, $R^8$, and $R^9$ are hydrogen or $R^1$ and $R^2$ together form a ketone, $R^3$, $R^4$, $R^6$, $R^{10}$ and $R^{11}$ are as defined herein and $R^7$ is carboxymethyl.

In still another conversion, the compound of formula Ia in which $R^1$, $R^2$, $R^5$, $R^7$, $R^8$ and $R^9$ are hydrogen or $R^1$ and $R^2$ together form a ketone and $R^3$, $R^4$, $R^6$, $R^{10}$ and $R^{11}$ are as defined herein is reacted with a compound of formula $X-CO-(CH_2)_{n-1}-X^1$ in which n, X and $X^1$ are as defined herein followed by amination with an amine of formula $HNR^{12}R^{13}$ in which $R^{12}$ $R^{13}$ are as defined herein, in the same manner as described above, to obtain the corresponding compound of formula Ia in which $R^1$, $R^2$, $R^5$, $R^8$ and $R^9$ are hydrogen or $R^1$ and $R^2$ together form a ketone, $R^3$, $R^4$, $R^6$, $R^{10}$ and $R^{11}$ are as defined herein and $R^7$ is a radical of formula $CO-(CH_2)_{n-1}NR^{12}R^{13}$ wherein n, $R^{12}$ and $R^{13}$ are as defined herein.

Reduction of the latter compound of formula Ia, in the same manner as described above, gives the corresponding compound of formula Ia in which $R^1$, $R^2$, $R^5$, $R^8$ and $R^9$ are hydrogen or $R^1$ and $R^2$ together form a ketone, $R^3$, $R^4$, $R^6$, $R^{10}$ and $R^{11}$ are as defined herein and $R^7$ is a radical of formula $(CH_2)_nNR^{12}R^{13}$ wherein n, $R^{12}$ and $R^{13}$ are as defined herein.

Reaction of the compound of formula Ia in which $R^1$, $R^2$, $R^5$, $R^7$, $R^8$ and $R^9$ are hydrogen or $R^1$ and $R^2$ together form a ketone and $R^3$, $R^4$, $R^6$, $R^{10}$ and $R^{11}$ are as defined herein with cyanogen bromide followed by alkaline hydrolysis, in the same manner as described above, gives the corresponding compound of formula Ia in which $R^1$, $R^2$, $R^5$, $R^8$ and $R^9$ are hydrogen or $R^1$ and $R^2$ together form a ketone, $R^3$, $R^4$, $R^6$, $R^{10}$ and $R^{11}$ are as defined herein and $R^7$ is aminocarbonyl.

(b) Preparation of the compounds of formula Ib

Reaction scheme 4 illustrates a process for the preparation of the compounds of formula Ib in which $R^3$ and $R^4$ each is hydrogen, lower alkoxy, lower alkyl, halo or hydroxy; or $R^3$ and $R^4$ together form a OCH$_2$O chain; $R^{14}$, $R^{16}$ and $R^{17}$ are hydrogen; and $R^{15}$ is hydrogen or lower alkyl.

molar equivalents of hydroxylamine hydrochloride and about three molar equivalents of potassium hydroxide in a mixture of water and ethanol at 80° to 100° C. for five to 30 minutes to obtain the corresponding oxime of formula XVI in which $R^3$, $R^4$ and $R^{15}$ are as defined herein. The latter compound is reduced, preferably with nickel-aluminum alloy and sodium hydroxide in a mixture of water and ethanol at 20° to 30° C. for one to four hours, to obtain the corresponding amine of formula XVII in which $R^3$, $R^4$ and $R^{15}$ are as defined herein.

In addition to the above described process for preparing an amine of formula XVII, other processes are available for preparing an amine of formula XVII. For instance, a preferred process for preparing an amine of formula XVII in which $R^3$ and $R^4$ are as defined herein

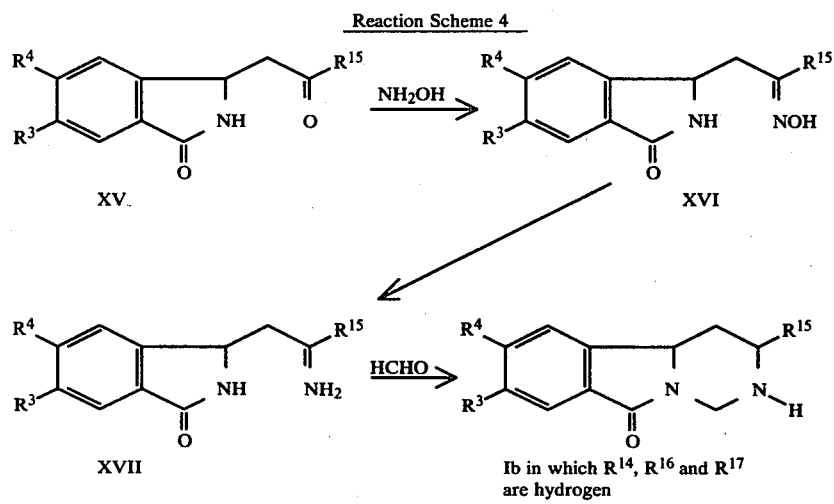

Reaction Scheme 4

The starting materials of formula XV in which $R^3$, $R^4$ and $R^{15}$ are as defined herein are obtained by the appropriate conversion of a 2,3-dihydro-3-oxo-1H-isoindole-1-acetic acid derivative, which also is known as a 1,3-dihydro-3-oxo-2H-isoindole-1-acetic acid derivative. The latter compounds are either known, for example 2,3-dihydro-3-oxo-1H-isoindole-1-acetic acid is described by F. M. Rowe et al., J. Chem. Soc., 1098 (1936), or can be prepared by an analogous process to that described in the latter reference. One conversion of the 2,3-dihydro-3-oxo-1H-isoindole-1-acetic acid derivatives is the reaction of the latter compound with four to six molar equivalents of a lower alkyl lithium in an inert organic solvent, preferably tetrahydrofuran and/or diethyl ether, at 20° to 30° C. for two to five hours to obtain the corresponding compound of formula XV in which $R^3$ and $R^4$ are as defined herein and $R^{15}$ is lower alkyl. Another conversion of the 2,3-dihydro-3-oxo-1H-isoindole-1-acetic acid derivative is the reduction of the latter compound to obtain the corresponding aldehyde of formula XV in which $R^3$ and $R^4$ are as defined herein and $R^{15}$ is hydrogen.

It is necessary to convert the compound of formula XV to the corresponding amine of formula XVII. A preferred method of achieving this conversion is to react the compound of formula XV with about two and $R^{15}$ is hydrogen is the hydrogenation of a corresponding derivative of 3-cyanomethylenephthalimidine with hydrogen under a pressure of 700 psi at 70° C. in the presence of Raney-nickel catalyst in a solvent of ethanol saturated with ammonia. The 3-cyanomethylenephthaimidine derivatives are either known, for example, 3-cyanomethylenephthalimidine is described by J. Kranz, Chem. Ber., 100, 2261 (1967), or can be prepared by an analogous process to that described in the latter reference.

Once again, returning to a reaction scheme 4, the amine of formula XVII is condensed with three to five molar equivalents of formaldehyde, preferably in the form of 37% aqueous formaldehyde, in an inert organic solvent, preferably ethanol, at 80° to 100° C. for two to five hours to obtain the corresponding compound of formula Ib in which $R^3$, $R^4$ and $R^{15}$ are as defined herein, and $R^{14}$, $R^{16}$ and $R^{17}$ are hydrogen.

In addition to the process illustrated in reaction scheme 4, another process for the preparation of the compounds of formula Ib in which $R^3$, $R^4$, $R^{14}$ and $R^{15}$ are as defined herein, and $R^{16}$ and $R^{17}$ are hydrogen or $R^{16}$ and $R^{17}$ together form an imine is illustrated in reaction scheme 5. In other words, with regard to the imine, when $R^{16}$ and $R^{17}$ are joined together forming a bond, a cyclic imine is provided.

Reaction Scheme 5

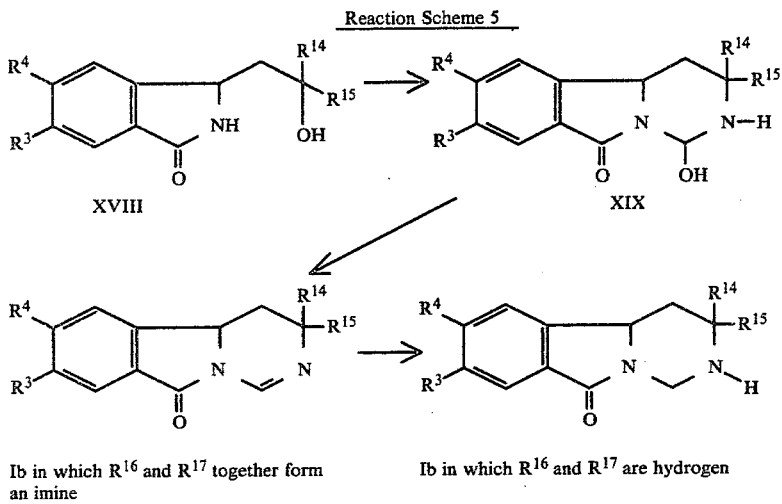

Ib in which $R^{16}$ and $R^{17}$ together form an imine

Ib in which $R^{16}$ and $R^{17}$ are hydrogen

With reference to reaction scheme 5, the starting materials of formula XVIII are obtained from the appropriate 2,3-dihydro-3-oxo-1H-isoindole-1-acetic acid derivative. For instance, reduction of the latter compound with a complex metal hydride, preferably lithium aluminum hydride or borane, in an inert organic solvent, preferably tetrahydrofuran or diethyl ether, at 0° to 30° C. for one to five hours gives the corresponding compound of formula XVIII in which $R^3$ and $R^4$ are as defined herein, and $R^{14}$ and $R^{15}$ are hydrogen. In another preparation of a compound of formula XVIII, the 2,3-dihydro-3-oxo-1H-isoindole-1-acetic acid derivative is esterified with a lower alkanol in the presence of an acid catalyst, preferably p-toluenesulfonic, at 60° to 80° C. for three to five hours to obtain the corresponding 2,3-dihydro-3-oxo-1H-isoindole-1-acetic acid lower alkyl ester derivative. Reaction of the latter compound with about two to ten molar equivalents of a lower alkyl magnesium halide, e.g. a lower alkyl magnesium chloride, bromide or iodide, in an inert organic solvent, preferably tetrahydrofuran and/or diethyl ether, at 30° to 50° C. for 3 to 30 hours gives the corresponding compound of formula XVIII in which $R^3$ and $R^4$ are as defined herein, and $R^{14}$ and $R^{15}$ each is the same lower alkyl.

The compounds of formula XV, described above and illustrated in reaction scheme 4, are also useful for preparing the alcohols of formula XVIII. For example, the compound of formula XV in which $R^3$ and $R^4$ are as defined herein and $R^{15}$ is lower alkyl are reduced with a complex metal hydride, preferably lithium aluminum hydride or sodium borohydride, to obtain the corresponding compound of formula XVIII in which $R^3$ and $R^4$ are as defined herein, $R^{14}$ is hydrogen and $R^{15}$ is lower alkyl. Another useful conversion of the compound of formula XV in which $R^3$ and $R^4$ are as defined herein and $R^{15}$ is lower alkyl is the reaction of the latter compound with about one to five molar equivalents of the Grignard reagent, $R^{14}$-magnesium halide, i.e. $R^{14}$-magnesium chloride, bromide or iodide, wherein $R^{14}$ is lower alkyl, in the same manner as described above, to obtain the corresponding compound of formula XVIII in which $R^3$ and $R^4$ are as defined herein, and $R^{14}$ and $R^{15}$ each is lower alkyl.

With reference to reaction scheme 5, the alcohol of formula XVIII is reacted with 1.5 to 2.0 molar equivalents of sodium cyanide in the presence of about 20 to 40 molar equivalents of sulfuric acid in a solvent of acetic acid at 20° to 30° C. for two to six hours to obtain the corresponding compound of formula XIX in which $R^3$, $R^4$, $R^{14}$ and $R^{15}$ are as defined herein.

Dehydration of the compound of formula XIX, preferably with 5 to 15 molar equivalents of thionyl chloride at 70° to 80° C. for one to five hours gives the corresponding hydrochloride salt of the compound of formula Ib in which $R^3$, $R^4$, $R^{14}$ and $R^{15}$ are as defined herein, and $R^{16}$ and $R^{17}$ together form an amine. If desired, the latter salt can be dissolved in a dilute solution of an aqueous alkali, preferably sodium hydroxide or sodium bicarbonate, and the solution is extracted with a water immiscible organic solvent, preferably ethyl acetate or chloroform, to obtain the corresponding compound of formula Ib in which $R^3$, $R^4$, $R^{14}$ and $R^{15}$ are as defined herein, and $R^{16}$ and $R^{17}$ together form an amine.

Reduction of the latter compound of formula Ib with a complex metal hydride, preferably with three to five molar equivalents of sodium borohydride in an inert organic solvent, preferably methanol, at 50° to 70° C. for one to three hours, gives the corresponding compound of formula Ib in which $R^3$, $R^4$, $R^{14}$ and $R^{15}$ are as defined herein, and $R^{16}$ and $R^{17}$ are hydrogen.

The compounds of formula Ib, prepared as described above, can be transformed to the compounds of formula Ib. For this transformation, the compound of formula Ib in which $R^{16}$ and $R^{17}$ are hydrogen is reacted with about 1.1 to 1.5 molar equivalents of a compound of formula $X-CO-(CH_2)_{n-1}-X^1$ wherein n is an integer from two to six, and X and $X^1$ each is chloro, bromo or iodo in the presence of an organic proton acceptor, preferably triethylamine, in an inert organic solvent, preferably benzene, at 20° to 30° C. for 10 to 30 hours to give the corresponding intermediate having the radical $CO-(CH_2)_{n-1}-X^1$ in which n and $X^1$ are as defined herein. Subsequently, the latter intermediate is reacted with about 5 to 15 molar equivalents of an amine of formula $HNR^{12}R^{13}$ in which $R^{12}$ and $R^{13}$ each is hydrogen or lower alkyl in an inert organic solvent, preferably tetrahydrofuran, at 20° to 60° C. for one to ten hours to obtain the corresponding compound of formula Ib in which $R^3$, $R^4$, $R^{14}$ and $R^{15}$ are as defined herein, $R^{16}$ is a radical of formula $CO(CH_2)_{n-1}NR^{12}R^{13}$ wherein n, $R^{12}$ and $R^{13}$ are as defined herein, and $R^{17}$ is hydrogen.

The latter compound of formula Ib can be reduced with a complex metal hydride, preferably with about five to ten molar equivalents of borane in an inert organic solvent, preferably tetrahydrofuran or dioxane, at 60° to 70° C. for 15 to 30 hours to obtain the corresponding compound of formula Ib in which $R^3$, $R^4$, $R^{14}$ and $R^{15}$ are as defined herein, $R^{16}$ is a radical of formula $(CH_2)_nNR^{12}R^{13}$ wherein n, $R^{12}$ and $R^{13}$ are as defined herein, and $R^{17}$ is hydrogen.

The following examples illustrate further this invention.

EXAMPLE 1

α-Bromo-2-carboxyphenylacetic Acid Diethyl Ester (III; $R^5$, $R^{18}$ and $R^{19}$=H and Alk=Et)

2-Carboxyphenylacetic acid (200 g, 1.11 mol) in ethanol (2000 ml) is saturated with anhydrous hydrogen chloride and refluxed for 16 hr. The solution is evaporated and water is added. The solution is extracted with chloroform and the chloroform extract is washed with 5% aqueous sodium bicarbonate and water, dried and evaporated to afford 2-carboxyphenylacetic acid diethyl ester (259 g).

The latter compound (247 g, 1.03 mol) is dissolved in dry carbon tetrachloride (2500 ml) and N-bromosuccinimide (198 g, 1.11 mol) is added. The solution is stirred at reflux for 1.5 hr while irradiating with a 500 watt photospot lamp and filtered. The filtrate is evaporated to give the title compound (280 g), nmr (CDCl$_3$) δ 1.35(m), 4.35(m), 6.65(s) and 7.3–8.1(m).

EXAMPLE 2

α-Bromo-2-carboxy-4,5-dimethoxyphenylacetic Acid Diethyl Ester (III: $R^5$=H, $R^{18}$ and $R^{19}$=OMe and Alk=Et)

Phosphorus pentoxide (500 g, 3.5 mol) is added portionwise to a mechanically stirred solution of 3-(3,4-dimethoxyphenyl)propionic acid (100 g, 0.67 mol) in benzene (2500 ml) and the mixture is refluxed for 8 hr. The reaction is slowly poured into ice-water, and the benzene layer is separated and washed with 10% sodium hydroxide and water, dried and evaporated to give 5,6-dimethoxyindan-1-one (60 g), mp 100° C., described by W. H. Perkin and R. Robinson, J. Chem. Soc., 1073 (1907).

A solution of the latter compound (5.0 g, 0.026 mol) and isoamyl nitrite (7.0 g, 0.06 mol) in methanol (15 ml) and conc. hydrochloric acid (3 ml) is stirred at 50° C. for 30 min. The yellow precipitate is collected and washed with methanol to obtain 5,6-dimethoxyindan-1,2-dione 2-oxime (3.1 g), mp 240° C., described by W. H. Perkin and R. Robinson, supra.

Phosphorus pentachloride (10 g, 0.048 mol) is added portionwise to a well stirring suspension of the latter oxime (3 g, 0.0136 mol) in diethyl ether (20 ml). The reaction is stirred for 1 hr and poured into ice-water. The organic phase is collected, washed with water, dried and evaporated to give a solid (2.1 g).

This solid is stirred at reflux with 50 ml of 20% sodium hydroxide for 1 hr. The reaction is filtered and the filtrate is acidified with 6 N hydrochloric acid. The resulting precipitate is collected and dried to obtain 2-carboxy-4,5-dimethoxyphenylacetic acid (2.1 g), mp 217°–219° C., described by W. H. Perkin and R. Robinson, supra.

A solution of the latter diacid (2.1 g, 0.00875 mol) in 200 ml of ethanol is saturated with hydrogen chloride and refluxed for 18 hr. Most of the ethanol is evaporated and chloroform is added. The solution is washed with 5% sodium bicarbonate and water, dried and evaporated. The oil is chromatographed on silica gel using acetone-benzene (1:9) and the eluates are evaporated to obtain crystals (1.24 g) of 2-carboxy-4,5-dimethoxyphenylacetic acid diethyl ester, mp 65°–67° C.

A mixture consisting of the latter diester (26.5 g, 0.09 mol) and N-bromosuccinimide (19.2 g, 0.108 mol) in dry carbontetrachloride (3000 ml) is stirred at reflux for 2 hr while irradiating with a 500 watt photospot bulb. The reaction is cooled in an ice-bath, filtered and evaporated. The residue is chromatographed on silica gel using acetone-benzene (1:9) and the eluates are evaporated to obtain an oil (29 g) of the title compound, nmr (CDCl$_3$) δ 1.32(t), 1.44(t), 3.95(s), 3.98(s), 4.4(q), 6.8(s), 7.45(s) and 7.53(s).

In the same manner but replacing 3-(3,4-dimethoxyphenyl) propionic acid with an equivalent amount of 3-(3,4-methylenedioxyphenyl) propionic acid or 3-(3,4-dichlorophenyl) propionic acid, or replacing 5,6-dimethoxyindan-1-one with an equivalent amount of 5-methoxyindan-1-one, or replacing 2-carboxy-4,5-dimethoxyphenylacetic acid with an equivalent amount of 2-carboxy-4-chlorophenylacetic acid [described by D. E. Ames and T. F. Grey, J. Chem. Soc., 3518(1966)] or 2-carboxy-4-methoxyphenylacetic acid [described by H. E. Ungnade et al., J. Org. Chem., 10, 533 (1945)], the following compounds of formula III are obtained, respectively: α-bromo-2-carboxy-3,4-methylenedioxyphenylacetic acid diethyl ester, α-bromo-2-carboxy-4,5-dichlorophenylacetic acid diethyl ester, α-bromo-2-carboxy-5-methoxyphenylacetic acid diethyl ester, α-bromo-2-carboxy-4-chlorophenylacetic acid diethyl ester and α-bromo-2-carboxy-4-methoxyphenylacetic acid diethyl ester.

EXAMPLE 3

2-Carboxy-α,4-dibromophenylacetic Acid Diethyl Ester (III: $R^5$ and $R^{19}$=H, $R^{18}$=Br and Alk=Et)

A mixture of 2-carboxy-4-nitrophenylacetic acid (described by H. E. Ungnade et al., J. Org. Chem., 10, 533 (1945), 50 g, 0.22 mol) and 5% palladium on carbon (5 g) is rapidly stirred under an atmosphere of hydrogen until the nitro group is reduced. Water (300 ml) is added and the mixture is warmed to dissolve the precipitate. The mixture is filtered through diatomaceous earth. The filtrate is evaporated and 375 ml of 2 N hydrobromic acid is added. The resulting solution is cooled in an ice-bath to 0°–5° C. Sodium nitrite (15.2 g, 0.22 mol) in 50 ml of water is added while stirring. The latter solution is added slowly to a cold (0°–5° C.) stirring freshly prepared solution of cuprous bromide (150 g, 0.105 mol) in 230 ml of 49% hydrobromic acid. The reaction is stirred at room temperature for 2 hr and the precipitate is collected by filtration. The precipitate is washed with water and dried to obtain 4-bromo-2-carboxyphenylacetic acid (53 g), mp 210°–213° C.

The latter diacid (52 g, 0.2 mol) is dissolved in anhydrous ethanol (1000 ml) saturated with hydrogen chloride. The solution is refluxed overnight and evaporated. The residue is dissolved in chloroform and the solution is washed with water, 5% sodium bicarbonate solution, dried and evaporated to afford 4-bromo-2-carboxyphenylacetic acid diethyl ester (66 g), nmr (CDCl$_3$) δ 1.23(t), 1.36(t), 4.0(s), 4.2(q), 4.4(q) and 7.1–8.3(m).

A solution of the latter diethyl ester (66 g, 0.2 mol) and N-bromosuccinimide (40 g, 0.22 mol) in carbon tetrachloride (4000 ml) in refluxed and irradiated with a 500 W photospot lamp for 4 hr. The reaction is cooled, filtered and evaporated. The oily residue is chromatographed on silica gel using benzene and the eluates are evaporated to obtain the title compound (75 g), nmr (CDCl$_3$) δ 1.25(t), 1.4(t), 4.3(q), 4.45(q), 6.55(s) and 7.7–8.2(m).

EXAMPLE 4

α-Bromo-2-carboxy-4-methoxymethyleneoxyphenylacetic Acid Diethyl Ester (III: R$^5$ and R$^{19}$=H, R$^{18}$=OCH$_2$OMe and Alk=Et)

A solution of 2-carboxy-4-hydroxyphenylacetic acid (described by H. E. Ungnade et al., supra, 28.4 g, 0.145 mol) in ethanol (3800 ml through which hydrogen chloride had been bubbled for 45 min) is refluxed for 4 hr. The reaction is cooled, more hydrogen chloride is bubbled in for 45 min and the reaction is refluxed again for 3.5 hr. The reaction is cooled, hydrogen chloride bubbled in and refluxed for a further 4 hr. The solution is evaporated and the residue is dissolved in benzene. This solution is washed with 5% sodium bicarbonate and water, dried and evaporated. The residue is chromatographed on silica gel using 10% acetone in benzene and the eluates are evaporated to obtain 2-carboxy-4-hydroxyphenylacetic acid diethyl ester (35 g), nmr (CDCl$_3$) δ 1.3(t), 1.42(t), 3.95(s), 4.25(q), 4.35(q), 6.7(s) and 6.75–7.5(m).

A solution of the latter phenolic diester (42.9 g, 0.17 mol) in 850 ml of benzene is added slowly to a stirring cool suspension of sodium hydride (9 g of a 50% dispersion in mineral oil, 0.18 mol). The mixture is stirred for 30 min at 22° C., cooled in an ice-bath and chloromethyl methyl ether (15 g, 0.18 mol) in 430 ml of benzene is added slowly. The reaction is stirred at 22° C. for 2.5 hrs, water is cautiously added and the layers are separated. The organic phase is washed with water, dried and evaporated. The residue is chromatographed on silica gel using 10% acetone in benzene and the eluates are evaporated to obtain 2-carboxy-4-methoxymethyleneoxyphenylacetic acid diethyl ester (48 g), nmr (CDCl$_3$) δ 1.2(t), 1.31(t), 3.5(s), 4.84(s), 4.1(q), 4.26(q), 5.08(s) and 7.0–7.6(m).

A stirring mixture of the latter diester (48 g, 0.162 mol) and N-bromosuccinimide (28.8 g, 0.162 mol) in carbon tetrachloride (2000 ml) is irradiated with a photospot lamp at reflux for 2 hr. The reaction is cooled, filtered and evaporated. The residue is chromatographed on silica gel using 5% ethyl acetate in benzene and the eluates are evaporated to give the title compound (40 g), nmr(CDCl$_3$) δ 1.29(t), 1.4(t), 3.38(s), 4.18(q), 4.31(q), 5.1(s), 6.4(s) and 7.0–8.8(m).

EXAMPLE 5

2-Carboxy-α-bromo-α-methylphenylacetic Acid Diethyl Ester (III: R$^5$=Me, R$^{18}$ and R$^{19}$=H and Alk=Et)

A solution of 2-carboxyphenylacetic acid diethyl ester (described in Example 1, 32.4 g, 0.135 mol) in 100 ml of benzene is added dropwise to stirring ice-cooled suspension of sodium hydride (6.6 g of a 50% dispersion in mineral oil, 0.14 mol) in 200 ml of benzene. A solution of methyl iodide (30 g, 0.21 mol) is added dropwise and the resulting mixture is refluxed for 18 hr. More methyl iodide (10 g, 0.07 mol) is added and refluxing is continued for 24 hr. The reaction is cooled, 50% aqueous acetic acid is added until the reaction is acidic (pH 6). The organic phase is collected, washed with water, dried, and evaporated. The residue is chromatographed on silica gel using 5% acetone in benzene and the eluates are evaporated to obtain 2-carboxy-α-methylphenylacetic acid diethyl ester (20 g), nmr (CDCl$_3$) δ 1.19(t), 1.40(t), 1.56(d), 4.16(q), 4.42(q), 4.71(q), 7.44(m) and 7.96(m).

A refluxing stirring mixture of the latter diethyl ester (72 g, 0.288 ml) and N-bromosuccinimide (52 g, 0.288 ml) in carbon tetrachloride (3600 ml) is irradiated with a 500 W photospot lamp for 3.5 hr. The reaction is cooled, filtered and evaporated. The residue is chromatographed on silica gel using 2% acetone in benzene and the eluates are evaporated to give the title compound (50 g), nmr (CDCl$_3$) δ 1.2(t), 1.32(t), 2.32(s), 4.16(q), 4.28(q) and 7.2–8.2(m).

EXAMPLE 6

3,4-Dihydropyrazino[2,1-a]isoindole-1,6(2H,10bH)-dione (V: R$^5$, R$^8$, R$^9$, R$^{10}$, R$^{11}$, R$^{18}$ and R$^{19}$=H)

α-Bromo-2-carboxyphenylacetic acid diethyl ester (described in Example 1, 280 g, 0.89 mol) in dry tetrahydrofuran (1100 ml) is added dropwise to a mixture of triethylamine (98 g, 0.97 mol) and ethylenediamine (112 g, 1.87 mol) in tetrahydrofuran (3000 ml) while stirring vigorously and refluxing over a 1.5 hr period.

Most of the solvent is evaporated and chloroform is added. This solution is washed with 10% hydrochloric acid and water, dried and evaporated to give a semi-solid residue. The residue is suspended in acetonitrile and the mixture is filtered. The precipitate is crystallized from acetonitrile to give the title compound (64 g), mp 220°–223° C., Anal. Calc'd. for C$_{11}$H$_{10}$N$_2$O$_2$: C, 65.33% H, 4.98% N, 13.86% and Found: C 65.10% H, 4.83% N, 13.94%.

In the same manner but replacing α-bromo-2-carboxyphenylacetic acid diethyl ester with an equivalent amount of α-bromo-2-carboxy-4,5-dimethoxy-phenylacetic acid diethyl ester (described in Example 2), α-bromo-2-carboxy-3,4-methylenedioxyphenylacetic acid diethyl ester (described in Example 2), α-bromo-2-carboxy-4,5-dichlorophenylacetic acid diethyl ester (described in Example 2), α-bromo-2-carboxy-5-methoxyphenylacetic diethyl ester (described in Example 2), α-bromo-2-carboxy-4-chlorophenylacetic acid diethyl ester (described in Example 2), α-bromo-2-carboxy-4-methoxyphenylacetic acid diethyl ester (described in Example 2), 2-carboxy-α,4-dibromophenylacetic acid diethyl ester (described in Example 3), α-bromo-2-carboxy-4-methoxymethyleneoxyphenylacetic acid diethyl ester (described in Example 4), 2-carboxy-α-bromo-α-methylphenylacetic acid diethyl ester (described in Example 5), 2-carboxy-α-bromo-4-methyl-α-propylphenylacetic acid diethyl ester, 2-carboxy-α-bromo-5-ethoxy-4-iodophenylacetic acid diethyl ester, 2-carboxy-α-bromo-α-ethyl-4-trifluoromethylphenylacetic acid diethyl ester, 2-carboxy-α-bromo-4-ethyl-5-propylphenylacetic acid diethyl ester, 2-carboxy-α-bromo-5-butyphenylacetic acid diethyl ester or 2-carboxy-α-bromo-4-butoxy-α-phenylmethyl-phenylacetic acid diethyl ester, the following compounds of formula V are obtained, respectively: 8,9-dimethoxy-3,4-dihydropyrazino[2,1-a]isoindol-1,6(2H,10bH)-dione, mp 235°–240° C., Anal. Calc'd. for C$_{13}$H$_{14}$N$_2$O$_4$: C, 59.54%

H, 5.38% N, 10.68% and Found: C, 58.64% H, 5.38% N, 10.40%; 8,9-methylenedioxy-3,4-dihydropyrazino[2,1-a]isoindol-1,6(2H,10bH)-dione, mp 230° C., Anal. Calc'd for $C_{12}H_{10}N_2O_4$: C, 58.54% and Found: C, 58.24% H, 4.24% N, 11.15%; 8,9-dichloro-10b-hydroxy-3,4-dihydropyrazino[2,1-a]isoindol-1,6(2H,10bH)-dione, mp 270°–271° C., Anal. Calc'd. for $C_{11}H_8Cl_2N_2O_3$: C, 46.01% H, 2.80% N, 9.76% and Found: C, 45.99% H, 2.80% N, 9.81%; 9-methoxy-3,4-dihydropyrazino[2,1-a]isoindol-1,6(2H,10bH)-dione, nmr (CDCl$_3$) δ 3.1–4.4(m), 3.88(s), 5.28(s), 7.0–7.9(m) and 8.18(m); 8-chloro-3,4-dihydropyrazino[2,1-a]isoindol-1,6(2H,10bH)-dione, mp 207°–209° C.; 8-methoxy-3,4-dihydropyrazino[2,1-a]isoindol-1,6(2H,10bH)-dione, mp 199°–202° C., Anal. Calc'd. for $C_{12}H_{12}N_2O_3$: C, 62.06% H, 5.21% N, 12.06% and Found: C, 61.38% H, 5.41% N, 11.64; 8-bromo-3,4-dihydropyrazino[2,1-a]isoindol-1,6(2H,10bH)-dione, mp 249°–252° C., Anal. Calc'd. for $C_{11}H_9BrN_2O_2$: C, 47.00% H, 3.22% N, 9.97% and Found: C, 46.91% H, 3.11% N, 10.29%; 8-methoxymethyleneoxy-3,4-dihydropyrazino[2,1-a]isoindol-1,6(2H,10bH)-dione, mp 172°–176° C., Anal. Calc'd. for $C_{13}H_{14}N_2O_4$: C, 59.53% H, 5.38% N, 10.68% and Found: C, 59.39% H, 5.52% N, 10.34%; 10b-methyl-3,4-dihydropyrazino[2,1-a]isoindol-1,6(2H,10bH)-dione, mp 165°–168° C., Anal. Calc'd. for $C_{12}H_{12}N_2O_2$: C, 66.65% H, 5.60% N, 12.96% and Found: C, 66.50% H, 5.64% N, 12.87; 8-methyl-10b-propyl-3,4-dihydropyrazino[2,1-a]isoindol-1,6(2H,10bH)-dione; 9-ethoxy-8-iodo-3,4-dihydropyrazino[2,1-a]isoindol-1,6(2H,10bH)-dione; 10b-ethyl-4-trifluoromethyl-3,4-dihydropyrazino[2,1-a]isoindol-1,6(2H,10bH)-dione; 4-ethyl-5-propyl-3,4-dihydropyrazino[2,1-a]isoindol-1,6(2H,10bH)-dione; 9-butyl-3,4-dihydropyrazino[2,1-a]isoindol-1,6(2H,10bH)-dione; and 8-butoxy-10b-phenylmethyl-3,4-dihydropyrazino[2,1-a]isoindol-1,6(2H,10bH)-dione.

In the same manner but replacing 1,2-ethanediamine with an equivalent amount of 2-methyl-1,2-propanediamine, 1,2-propanediamine, 1,2-cyclohexanediamine, N-phenylmethyl-1,2-ethanediamine, N-ethyl-1,2-propandiamine, N-phenylmethyl-1,2-butaneamine, 3,4-hexaneamine, 2,3-dimethyl-2,3-butaneamine or N-butyl-2,3-pentaneamine, the following compounds of formula V are obtained, respectively: 3,3-dimethyl-3,4-dihydropyrazino[2,1-a]isoindol-1,6(2H,10bH)-dione, mp 245°–248° C.; 3-methyl-3,4-dihydropyrazino[2,1-a]isoindol-1,6(2H,10bH)-dione, mp 205°–210° C., Anal. Calc'd. for $C_{12}H_{12}N_2O_2$: C, 66.65% H, 5.60% N, 12.96% and Found: C, 66.18% H, 5.60% N, 12.75%; 3,4-dimethyl-3,4-dihydropyrazino[2,1-a]isoindol-1,6(2H,10bH)-dione, mp 189°–193° C., Anal. Calc'd. for $C_{13}H_{14}N_2O_2$: C, 67.81% H, 6.13%, N, 12.17% and Found: C, 67.08% H, 6.14% N, 11.91%; 1,2,3,4,4a,5-,6a,12a-octahydroisoindolo[2,1-a]quinoxalin-6,11-dione isomer A, mp 235°–237° C., Anal. Calc'd. for $C_{15}H_{16}N_2O_2$: C, 70.29% H, 6.29% N, 10.93% and Found: C, 69.71% H, 6.28% N, 11.21%; and isomer B, Anal. Calc'd. for $C_{15}H_{16}N_2O_2$: C, 70.29% H, 6.29% N, 10.93% and Found: C, 70.44% H, 6.21% N, 11.08%; mp 180°–184° C., and 2-phenylmethyl-3,4-dihydropyrazino[2,1-a]isoindol-1,6(2H,10bH)-dione, mp 170°–171° C., Anal. Calc'd. for $C_{18}H_{16}N_2O_2$: C, 73.96% H, 5.52% N, 9.58% and Found: C, 73.85% H, 5.45% N, 9.97%; 2-ethyl-3-methyl-3,4-dihydropyrazino[2,1-a]isoindol-1,6(2H,10bH)-dione; 3-ethyl-2-phenylmethyl-3,4-dihydropyrazino[2,1-a]isoindol-1,6(2H,10bH)-dione; 3,4-diethyl-3,4-dihydropyrazino[2,1-a]isoindol-1,6(2H,10bH)-dione; 3,3,4,4-tetramethyl-3,4-dihydropyrazino[2,1-a]isoindol-1,6(2H,10bH)-dione and 2-butyl-3-ethyl-4-methyl-3,4-dihydropyrazino[2,1-a]isoindol-1,6(2H,10bH)-dione.

EXAMPLE 7

1,2,3,4,6,10b-Hexahydropyrazino[2,1-a]isoindole(Ia: $R^1,R^2,R^3,R^4,R^5,R^6,R^7,R^8,R^9,R^{10}$ and $R^{11}$=H)

3,4-Dihydropyrazino[2,1-a]isoindole-1,6(2H,10bH)-dione (described in Example 6, 14 g, 0.0674 mol) is added portionwise to 700 ml of 1 M borane in tetrahydrofuran over a 0.5 hr period and then refluxed with stirring for 18 hr. The reaction is cooled, water is added dropwise until the hydrolysis is complete and then 140 ml of 6 N hydrochloric acid is added cautiously. Most of the tetrahydrofuran is distilled off until the distillation temperature reaches 90° C. Then 6 N sodium hydroxide (140 ml) is added and the solution is extracted with chloroform. The chloroform extract is washed with water, dried and evaporated to give the title compound (10 g), nmr (CDCl$_3$) δ 2.63(s), 2.6–4.3(m) and 7.3(m). The title compound is treated with a solution of hydrogen bromide in diethyl ether to give a solid. The solid is crystallized from ethanol to obtain the hydrobromide salt of the title compound, mp 155°–160° C. The title compound (8.9 g) is dissolved in a solution of ethanol containing maleic acid (6.45 g), charcoal is added and the mixture is filtered. The filtrate is evaporated and the residue is crystallized from ethanol-diethyl ether to obtain the maleate salt of the title compound, mp 133°–136° C., Anal. Calc'd. for $C_{11}H_{14}N_2.C_4H_4O_4$: C, 62.06%, H, 6.25% N, 9.65% and Found: C, 62.00% H, 6.29% N, 9.70%.

In the same manner but replacing 3,4-dihydropyrazino[2,1-a]isoindole-1,6(2H,10bH)-dione with an equivalent amount of another compound of formula V described in Example 6, the following compounds of formula Ia are obtained, respectively: 8,9-dimethoxy-1,2,3,4,6,10b-hexahydropyrazino[2,1-a]isoindole, maleate salt, mp 141°–144° C., Anal. Calc'd. for $C_{13}H_{18}N_2O_2.C_4H_4O_4$: C, 58.27% H, 6.33% N, 8.00% and Found: C, 58.04% H, 6.24% N, 8.07%; 5,7,8,9,10,10b-hexahydro-1,3-dioxolo[4,5-f]pyrazino[2,1-a]isoindole, nmr (DMSO-d$_6$) δ2.2–4.05(m), 5.9(s), 6.75(s) and 6.8(s), dihydrochloride salt, mp 212°–215° C., Anal. calc'd for C;hd 12H$_4$N$_2$O$_2$.2HCl: C, 46.61% H, 5.87% N, 9.06% and Found- C, 46.72% H, 5.90% N, 8.85%; 8,9-dichloro-1,2,3,4,6,10b-hexahydropyrazino[2,1-a]isoindole, dimaleate salt, mp 141°–143° C., Anal. Calc'd. for $C_{12}H_{16}N_2O.2C_4H_4O_4$:C, 55.04% H, 5.54% N, 6.42% and Found: C, 54.85% H, 5.65% N, 6.30%; 9-methoxy-1,2,3,4,6,10b-hexahydropyrazino[2,1-a]isoindole, nmr (CDCl$_3$) δ2.96(m), 3.71(m), 3.76(s), 3.40(d), 4.04(d) and 6.74(m), dimaleate salt, mp 147°–148° C., Anal. Calc'd. for $C_{12}H_{16}N_2O.2C_4H_4O_4$: C, 55.04% H, 5.54% N, 6.42% and Found: C, 54.85% H, 5.65% N, 6.30%; 8-chloro-1,2,3,4,6,10b-hexahydropyrazino[2,-1-a]isoindole, dihydrobromide salt, mp 145°–149° C., Anal. Calc'd. for $C_{11}H_{13}ClN_2.2HBr$: C, 35.65%, H, 4.08% N, 7.56% and Found: C, 35.21% H, 4.23% N, 7.61%; 8-methoxy-1,2,3,4,6,10b-hexahydropyrazino[2,1-a]isoindole, dimaleate salt, mp 126°–127° C., Anal. Calc'd. for $C_{12}H_{16}N_2O.2C_4H_4O_4$: C, 55.04% H, 5.54% N, 6.42% and Found: C, 55.04% H, 5.48% N, 6.50%; 8-bromo-1,2,3,4,6,10b-hexahydropyrazino[2,1-a]isoindole, nmr (CDCl$_3$) δ2.58(s), 2.50–4.3(m), 6.98(d), 7.35(d) and 7.40(s), maleate salt, mp 145°–148° C., Anal. Calc'd. for C$_{11}$H$_{13}$BrN$_2$.C$_4$H$_4$O$_4$: C, 48.79% H, 4.64% N, 7.59% and Found: C, 48.99% H, 4.78% N, 7.67%; 8-hydroxy-1,2,3,4,6,10b-hexahydropyrazino[2,1-a]isoindole, dimaleate salt, mp 150°–154° C., Anal. Calc'd. for C$_{11}$H$_{14}$N$_2$O.2C$_4$H$_4$O$_4$: C, 54.02% H, 5.25% N, 6.63% and Found: C, 54.12% H, 5.46% N, 6.32%; 10b-methyl-1,2,3,4,6,10b-hexahydropyrazino[2,1-a]isoindole; 8-methyl-10b-propyl-1,2,3,4,6,10b-hexahydropyrazino[2,1-a]isoindole; 9-ethoxy-8-iodo-1,2,3,4,6,10b-hexahydropyrazino[2,1-a]isoindole, 10b-ethyl-4-trifluoromethyl-1,2,3,4,6,10b-hexahydropyrazino[2,1-a]isoindole; 4-ethyl-5-propyl-1,2,3,4,6,10b-hexahydropyrazino[2,1-a]isoindole; 9-butyl-1,2,3,4,6,10b-hexahydropyrazino[2,1-a]isoindole; 8-butoxy-10b-phenylmethyl-1,2,3,4,6,10b-hexahydropyrazino[2,1-b]isoindole; 3,3-dimethyl-1,2,3,4,6,10b-hexahydropyrazino[2,1-a]isoindole, nmr (DMSO-d$_6$) δ1.04(s), 1.15(s), 2.0–4.25(m) and 7.22(m), dimaleate salt, mp 166°–168° C., Anal. Calc'd. for C$_{13}$H$_{13}$N$_2$.2C$_4$H$_4$O$_4$: C, 58.05% H, 6.03% N, 6.45% and Found: C, 57.99% H, 6.04% N, 6.39%; 3-methyl-1,2,3,4,6,10b-hexahydropyrazino[2,1-a]isoindole, nmr (DMSO-d$_6$) δ0.94(d), 2.0–4.25(m) and 7.19(m), dimaleate salt, mp 133°–136° C., Anal. Calc'd. for C$_{12}$H$_{16}$N$_2$.2C$_4$H$_4$O$_4$: C, 57.13% H, 5.75% N, 6.66% and Found: C, 57.07% H, 5.60% N, 6.61%; 3,4-dimethyl-1,2,3,4,6,10b-hexahydropyrazino[2,1-a]isoindole, dihydrobromide salt, mp 305°–310° C., Anal. Calc'd. for C$_{13}$H$_{18}$N$_2$.2HBr: C, 42.87% H, 5.53% N, 7.69% and Found: C, 43.02% H, 5.47% N, 7.77%; 1,2,3,4,4a,5,6,6a,11,12a-decahydroisoindolo[2,1-a]quinoxaline malic acid salt, mp 155°–158° C., Anal. Calc'd. for C$_{15}$H$_{20}$N$_2$.C$_4$H$_6$O$_5$: C, 62.96% H, 7.23% N, 7.73% and Found: C, 62.69% H, 7.13% N, 8.14%; 2-phenylmethyl-1,2,3,4,6,10b-hexahydropyrazino[2,1-a]isoindole, hydrobromide salt, mp 252°–253° C.; 2-ethyl-3-methyl-1,2,3,4,6,10b-hexahydropyrazino[2,1-a]isoindole; 3-ethyl-2-phenylmethyl-1,2,3,4,6,10b-hexahydropyrazino[2,1-a]isoindole; 3,4-diethyl-1,2,3,4,6,10b-hexahydropyrazino[2,1-a]isoindole; 3,3,4,4-tetramethyl-1,2,3,4,6,10b-hexahydropyrazino[2,1-a]isoindole and 2-butyl-3-ethyl-4-methyl-1,2,3,4,6,10b-hexahydropyrazino[2,1-a]isoindole.

EXAMPLE 8

1,2,3,4,6,10b-Hexahydropyrazino[2,1-a]isoindol-6-one (Ia: R$^1$ and R$^2$ together form a ketone; R$^3$, R$^4$, R$^5$, R$^6$, R$^7$, R$^8$, R$^9$, R$^{10}$ and R$^{11}$=H)

3,4-Dihydropyrazino[2,1-a]isoindole-1,6(2H, 10bH)-dione (described in Example 6, 5.05 g, 0.025 mol) is added portionwise to 75 ml of 0.98 M borane in tetrahydrofuran. More tetrahydrofuran (75 ml) is added and the solution is stirred at room temperature for 4 hr. Water is cautiously added and the solution is acidified with 50 ml of 6 N hydrochloric acid. Most of the tetrahydrofuran is distilled off until the temperature of the vapours reaches 90° C. The reaction is cooled, made alkaline with 80 ml of 6 N sodium hydroxide and extracted with chloroform. The chloroform extract is washed with water, dried, and evaporated to give the title compound (4.37 g), nmr (DMSO-d$_6$) δ2.7–5.0(m) and 7.8(m). The title compound is dissolved in a solution of ethanol containing maleic acid and the solution is evaporated. The residue is crystallized from ethanol-diethyl ether to obtain the maleate salt (3.8 g) of the title compound, mp 190°–192° C., Anal. Calc'd. for C$_{11}$H$_{12}$N$_2$O.C$_4$H$_4$O$_4$: C, 59.20% H, 5.30% N, 9.21% and Found: C, 59.12% H, 5.28% N, 9.05%.

In the same manner but replacing 3,4-dihydropyrazino[2,1-a]isoindole-1,6-(2H,10bH)-dione with an equivalent amount of another compound of formula V described in Example 6, the following compounds of formula Ia are obtained, respectively: 8,9-dimethoxy-1,2,3,4,6,10b-hexahydropyrazino[2,1-a]isoindol-6-one; 8,9-methylenedioxy-1,2,3,4,6,10b-hexahydropyrazino[2,1-a]isoindol-6-one; 8,9-dichloro-1,2,3,4,6,10b-hexahydropyrazino[2,1-a]isoindol-6-one; 9-methoxy-1,2,3,4,6,10b-hexahydropyrazino[2,1-a]isoindol-6-one; 8-chloro-1,2,3,4,6,10b-hexahydropyrazino[2,1-a]isoindol-6-one; 8-methoxy-1,2,3,4,6,10b-hexahydropyrazino[2,1-a]isoindol-6-one, nmr (DMSO-d$_6$) δ2.0–4.5(m), 3.85(s) and 7.0–7.6(m), maleate salt, mp 161°–163° C., Anal. Calc'd. for C$_{12}$H$_{12}$N$_2$O$_2$.C$_4$H$_4$O$_4$: C, 57.48% H, 5.43% N, 8.38% and Found: C, 57.37% H, 5.44% N, 8.35%; 8-hydroxy-1,2,3,4,6,10b-hexahydropyrazino[2,1-a]isoindol-6-one, 10b-methyl-1,2,3,4,6,10b-hexahydropyrazino[2,1-a]isoindol-6-one; 8-methyl-10b-propyl-1,2,3,4,6,10b-hexahydropyrazino[2,1-a]isoindol-6-one; 9-ethoxy-8-iodo-1,2,3,4,6,10b-hexahydropyrazino[2,1-a]isoindol-6-one; 10b-ethyl-4-trifluoromethyl-1,2,3,4,6,10b-hexahydropyrazino[2,1-a]isoindol-6-one; 4-ethyl-5-propyl-1,2,3,4,6,10b-hexahydropyrazino[2,1-a]isoindol-6-one; 9-butyl-1,2,3,4,6,10b-hexahydropyrazino[2,1-a]isoindol-6-one; 8-butoxy-10b-phenylmethyl-1,2,3,4,6,10b-hexahydropyrazino[2,1-a]isoindol-6-one; 3,3-dimethyl-1,2,3,4,6,10b-hexahydropyrazino[2,1-a]isoindol-6-one; nmr (DMSO-d$_6$) δ0.88(s), 1.12(s), 2.52(s), 2.2–4.6(m) and 7.65(m), maleate salt, mp 220°–223° C., Anal. Calc'd. for C$_{13}$H$_{16}$N$_2$O.C$_4$H$_4$O$_4$: C, 61.43% H, 6.06% N, 8.43% and Found: C, 61.63% H, 6.09% N, 8.14%; 3-methyl-1,2,3,4,6,10b-hexahydropyrazino[2,1-a]isoindol-6-one, nmr (DMSO-d$_6$) δ1.10(d), 2.11(2d), 3.67(2d), 2.74(t), 4.2(d), 4.45(2d) and 7.67(m), maleate salt, mp 181°–184° C., Anal. Calc'd. for C$_{12}$H$_{13}$N$_2$O.C$_4$H$_4$O$_4$: C, 60.56% H, 5.40% N, 8.83% and Found: C, 60.18% H, 5.63% N, 8.72%; 3,4-dimethyl-1,2,3,4,6,10b-hexahydropyrazino[2,1-a]isoindol-6-one, isomer A, nmr (DMSO-d$_6$) δ1.0(d), 1.16(d), 1.9–2.8(m), 3.5(d), 3.6(d), 4.05–4.64(m) and 7.3–7.8(m), maleate salt, mp 197°–198° C., Anal. Calc'd. for C$_{13}$H$_{16}$N$_2$O.C$_4$H$_4$O$_4$: C, 61.43% H, 6.07% N, 8.43% and Found: C, 61.66% H, 6.13% N, 8.61%; and isomer B, maleate salt, mp 170°–172° C., Anal. Calc'd. for C$_{13}$H$_{16}$N$_2$O.C$_4$H$_4$O$_4$: C, 61.43% H, 6.07% N, 8.43% and Found: C, 61.24% H, 6.04% N, 8.51%; 1,2,3,4,4a,5,6,6a,11,12a-decahydroisoindolo[2,1-a]quinoxalin-11-one; 2-phenylmethyl-1,2,3,4,6,10b-hexahydropyrazino[2,1-a]isoindol-6-one; 2-ethyl-3-methyl-1,2,3,4-6,10b-hexahydropyrazino[2,1-a]isoindol-6-one, 3-ethyl-2-phenylmethyl-1,2,3,4,6,10b-hexahydropyrazino[2,1-a]isoindol-6-one, 3,4-diethyl-1,2,3,4,6,10b-hexahydropyrazino[2,1-a]isoindol-6-one, 3,3,4,4-tetramethyl-1,2,3,4,6,10b-hexahydropyrazino[2,1-a]isoindol-6-one and 2-butyl-3-ethyl-4-methyl-1,2,3,4,6,10b-hexahydropyrazino[2,1-a]isoindol-6-one.

EXAMPLE 9

1,2,3,4,6,10b-Hexahydropyrazino[2,1-a]isoindol-2-carboxamide (Ia: R$^1$, R$^2$, R$^3$, R$^4$, R$^5$, R$^6$, R$^8$, R$^9$, R$^{10}$ and R$^{11}$=H and R$^7$=CONH$_2$)

Cyanogen bromide (9.75 g, 0.092 mol) in 100 ml of tetrahydrofuran is added dropwise to a stirring ice-cooled solution of 1,2,3,4,6,10b-hexahydropyrazino[2,1-a]isoindole (described in Example 7, 16 g, 0.092 mol) and triethylamine (9.25 g, 0.092 mol) in 600 ml of tetrahydrofuran. The ice-bath is removed and the reaction is stirred at room temperature for one hr. Most of the solvent is evaporated off and water is added. The solution is extracted with chloroform. The chloroform extract is washed with water, dried and evaporated to afford an oil. A solution of the latter oil in 20% sodium hydroxide (650 ml) is refluxed for 2 hr and extracted with chloroform. The chloroform extract is washed with water, dried and evaporated. The residue is crystallized from benzene to obtain the title compound (4.9 g), mp 122°–125° C., Anal. Calc'd. for $C_{12}H_{15}N_3O$: C, 66.34% H, 6.96% N, 19.34% and Found: C, 66.05% H, 7.03% N, 19.32%.

EXAMPLE 10

1,2,3,4,6,10b-Hexahydro-2-methylpyrazino[2,1-a]isoindole (Ia: $R^1$, $R^2$, $R^3$, $R^4$, $R^5$, $R^6$, $R^8$, $R^9$, $R^{10}$ and $R^{11}$=H, and $R^7$=Me)

Ethyl chloroformate (5.7 g, 0.0525 mol) in benzene (80 ml) is added dropwise to a stirring solution of 1,2,3,4,6,10b-hexahydropyrazino[2,1-a]isoindole (described in Example 7, 8 g, 0.046 mol) and triethylamine (6.6 g, 0.065 mol) in benzene (300 ml) cooled in an ice-bath. The solution is stirred for 45 min and water (300 ml) is added. The organic layer is separated and washed with 5% sodium hydroxide and water, dried and evaporated to afford 11 g of oil. A solution of the latter oil in tetrahydrofuran (100 ml) is added dropwise to a stirring mixture of lithium aluminum hydride (11 g, 0.29 mol) in tetrahydrofuran (500 ml) and stirring continued for 45 min. The reaction is cooled in an ice-bath and ethyl acetate is added dropwise, followed by water. The mixture is filtered through diatomaceous earth and the filtrate is evaporated. The residue is dissolved in chloroform and the solution is washed with water, dried and evaporated to give the title compound (6 g), nmr (CDCl$_3$) δ2.38(s), 3.70(d), 4.18(d), 5.0(m) and 7.25(m). The title compound is treated with hydrogen chloride in diethyl ether and the solution is evaporated. The residue is crystallized from ethanol to obtain the dihydrochloride salt (4 g) of the title compound, mp 270°–275° C., Anal. Calc'd. for $C_{12}H_{16}N_2.2HCl$: C, 55.17% H, 6.59% N, 10.73% and Found: C, 54.45% H, 6.87% N, 10.58%.

In the same manner but replacing 1,2,3,4,6,10b-hexahydropyrazino[2,1-a]isoindole with an equivalent amount of another compound of formula Ia in which $R^7$ is hydrogen, described in Example 7, the following compounds of formula Ia are obtained, respectively: 2-methyl-8,9-dimethoxy-1,2,3,4,6,10b-hexahydropyrazino[2,1-a]isoindole, 2-methyl-1,2,3,4,6,10b-hexahydropyrazino[2,1-a]isoindole, 8,9-methylenedioxy-2-methyl-1,2,3,4,6,10b-hexahydropyrazino[2,1-a]isoindole, 8,9-dichloro-2-methyl-1,2,3,4,6,10b-hexahydropyrazino[2,1-a]isoindole, 9-methoxy-2-methyl-1,2,3,4,6,10b-hexahydropyrazino[2,1-a]isoindole, 8-chloro-2-methyl-1,2,3,4,6,10b-hexahydropyrazino[2,1-a]isoindole, 8-methoxy-2-methyl-1,2,3,4,6,10b-hexahydropyrazino[2,1-a]isoindole, 8-bromo-2-methyl-1,2,3,4,6,10b-hexahydropyrazino[2,1-a]isoindole, 8-hydroxy-2-methyl-1,2,3,4,6,10b-hexahydropyrazino[2,1-a]isoindole, 2,10b-dimethyl-1,2,3,4,6,10b-hexahydropyrazino[2,1-a]isoindole, 2,8-dimethyl-10b-propyl-1,2,3,4,6,10b-hexahydropyrazino[2,1-a]isoindole, 9-ethoxy-8-iodo-2-methyl-1,2,3,4,6,10b-hexahydropyrazino[2,1-a]isoindole, 10b-ethyl-2-methyl-4-trifluoromethyl-1,2,3,4,6,10b-hexahydropyrazino[2,1-a]isoindole, 4-ethyl-2-methyl-5-propyl-1,2,3,4,6,10b-hexahydropyrazino[2,1-a]isoindole, 9-butyl-2-methyl-1,2,3,4,6,10b-hexahydropyrazino[2,1-a]isoindole, 8-butoxy-2-methyl-10b-phenylmethyl-1,2,3,4,6,10b-hexahydropyrazino[2,1-a]isoindole, 2,3,3-trimethyl-1,2,3,4,6,10b-hexahydropyrazino[2,1-a]isoindole, 2,3-dimethyl-1,2,3,4,5,10b-hexahydropyrazino[2,1-a]isoindole, 2,3,4-trimethyl-1,2,3,4,6,10b-hexahydropyrazino[2,1-a]isoindole, 5-methyl-1,2,3,4,4a,5,6,6a,11,12a-decahydroisoindolo[2,1-a]quinoxaline, 3,4-diethyl-2-methyl-1,2,3,4,6,10b-hexahydropyrazino[2,1-a]isoindole and 2,3,3,4,4-pentamethyl-1,2,3,4,6,10b-hexahydropyrazino[2,1-a]isoindole.

EXAMPLE 11

10b-Phenylmethyl-1,2,3,4,6,10b-hexahydropyrazino[2,1-a]isoindole (Ia: $R^1$, $R^2$, $R^3$, $R^4$, $R^6$, $R^7$, $R^8$, $R^9$, $R^{10}$ and $R^{11}$=H, and $R^5$=phenylmethyl)

3,4-Dihydropyrazino[2,1-a]isoindole-1,6(2H, 10bH)-dione (described in Example 6, 10 g, 0.049 mol) is added portionwise to a stirring mixture of 10% palladium on carbon (10 g) in 375 ml of dry toluene. The mixture is refluxed for 20 hr and filtered through Celite (diatomaceous earth). The filtrate is evaporated. The residue is chromatographed on silica gel using acetone-benzene (1:1) and the eluates are evaporated. The residue (5.0 g) is crystallized from acetone-petroleum ether to obtain 10b-phenylmethyl-3,4-dihydropyrazino[2,1-a]isoindole-1,6(2H, 10bH)-dione, mp 202°–204° C., Anal. Calc'd. for $C_{18}H_{16}N_2O_2$: C, 73.95% H, 5.52% N, 9.59% and Found: C, 74.18% H, 5.72% N, 9.57%.

The latter compound (8.0 g, 0.027 mol) is added portionwise to 240 ml of 1M borane in tetrahydrofuran and the solution is refluxed with stirring for 30 hr. The reaction is cooled and water is added until foaming ceases, followed by 120 ml of 6 N hydrochloric acid. The solvent is removed by distillation until the distillation head reaches 90° C. The residue is made alkaline with 6 N sodium hydroxide and extracted with chloroform. The chloroform extract is washed with water, dried and evaporated to give the title compound (8.9 g). The maleate salt, prepared as described in Example 8, melts at 151°–153° C., Anal. Calc'd. for $C_{18}H_{20}N_2.C_4H_4O_4$: C, 69.45% H, 6.36% N, 7.36% and Found: C, 69.60% H, 6.40% N, 7.39%.

EXAMPLE 12

2-Acetyl-1,2,3,4,6,10b-hexahydropyrazino[2,1-a]isoindol-6-one (Ia: $R^1$ and $R^2$ together form a ketone; $R^3$, $R^4$, $R^5$, $R^6$, $R^8$, $R^9$, $R^{10}$ and $R^{11}$=H, and $R^7$=COMe)

A solution consisting of 1,2,3,4,6,10b-hexahydropyrazino[2,1-a]isoindol-6-one (described in Example 8, 102 mg, 0.00054 mol), triethylamine (56 mg, 0.00055 mol) and acetyl chloride (44 mg, 0.00055 mol) in 10 ml of benzene is stirred at 10° C. for 5 min. Chloroform (50 ml) is added and the solution is washed with water, dried and evaporated. The residue is chromatographed on silica gel using 70% acetone in benzene and the eluates are evaporated to give the title compound (49 mg), mp 129°–131° C.

In the same manner but replacing 1,2,3,4,6,10b-hexahydropyrazino[2,1-a]isoindole-6-one with an equivalent amount of 1,2,3,4,6,10b-hexahydropyrazino-[2,1- a]isoindole (described in Example 7), 2-acetyl-1,2,3,4,6,10b-hexahydropyrazino[2,1-a]isoindole, nmr (CDCl$_3$) δ2.05(s), 5.1–5.6(m) and 7.4–8.1(m), is obtained.

Similarly, by replacing acetyl chloride with an equivalent amount of cyclohexylcarbonyl chloride or p-nitrobenzoyl chloride, the following compounds of formula Ia are obtained, respectively: 2-cyclohexylcarbonyl-1,2,3,4,6,10b-hexahydropyrazino[2,1-a]isoindol-6-one, mp 170°–175° C., Anal. Calc'd. for C$_{18}$H$_{22}$N$_2$O$_2$: C, 72.45% H, 7.43% N, 9.39% and Found: C, 72.70% H, 7.48% N, 9.44%, and 2-(4-nitrobenzoyl)-1,2,3,4,6,10b-hexahydropyrazino[2,1-a]isoindol-6-one, mp 242°–245° C., Anal. Calc'd. for C$_{18}$N$_{15}$N$_3$O$_4$: C, 64.09% H, 4.48% N, 12.46% and Found: C, 63.93% H, 4.54% N, 12.54%.

Similarly, by replacing acetyl chloride with an equivalent amount of cyclohexylcarbonyl chloride and replacing 1,2,3,4,6,10b-hexahydropyrazino[2,1-a]isoindol-6-one with an equivalent amount of 1,2,3,4,6,10b-hexahydropyrazino[2,1-a]isoindole (described in Example 7), 2-(cyclohexylcarbonyl)-1,2,3,4,6,10b-hexahydropyrazino[2,1-a]isoindole, mp 118°–120° C., Anal. Calc'd. for C$_{18}$H$_{24}$N$_2$O: C, 76.01% H, 8.51% N, 9.85% and Found: C, 75.62% H, 8.38% N, 9.89% is obtained.

EXAMPLE 13

2-Methyl-1,2,3,4,6,10b-hexahydropyrazino[2,1-a]isoindole-6-one (Ia: R$^1$ and R$^2$ together form a ketone; R$^3$, R$^4$, R$^5$, R$^6$, R$^8$, R$^9$, R$^{10}$ and R$^{11}$=H, and R$^7$=Me)

A solution of 1,2,3,4,6,10b-hexahydropyrazino[2,1-a]isoindol-6-one (described in Example 8, 2.25 g, 0.012 mol) in 90% formic acid (3.0 g, 0.06 mol) and 37% formaldehyde (2.5 g, 0.03 mol) is heated at 95°–105° C. for 8 hr. After cooling, the reaction is diluted with water, made alkaline with 6 N sodium hydroxide and extracted with benzene. The organic extract is washed with water, dried, and evaporated to afford the title compound (1.9 g), nmr (DMSO-d$_6$) δ1.2–2.0(m), 2.3(s), 2.7–4.35(m), 4.44(d), 4.63(d) and 7.2–7.8(m).

The hydrobromide salt of the title compound is prepared as described in Example 7 and crystallized from ethanol, 1.75 g, mp 290°–294° C., Anal. Calc'd. for C$_{12}$H$_{14}$N$_2$O.HBr: C, 50.89% H, 5.34% N, 9.89% and Found: C, 50.54% H, 5.69% N, 9.57%.

In the same manner but replacing 1,2,3,4,6,10b-hexahydropyrazino[2,1-a]isoindole with an equivalent amount of another compound of formula Ia in which R$^7$ is hydrogen, described in Example 8, the following compounds of formula Ia are obtained respectively: 2-methyl-8,9-dimethoxy-1,2,3,4,6,10b-hexahydropyrazino[2,1-a]isoindole-6-one, 2-methyl-1,2,3,4,6,10b-hexahydropyrazino[2,1-a]isoindole-6-one, 8,9-methylenedioxy-2-methyl-1,2,3,4,6,10b-hexahydropyrazino[2,1-a]isoindole-6-one, 8,9-dichloro-2-methyl-1,2,3,4,6,10b-hexahydropyrazino[2,1-a]isoindole-6-one, 9-methoxy-2-methyl-1,2,3,4,6,10b-hexahydropyrazino[2,1-a]isoindole-6-one, 8-chloro-2-methyl-1,2,3,4,6,10b-hexahydropyrazino[2,1-a]isoindole-6-one, 8-methoxy-2-methyl-1,2,3,4,6,10b-hexahydropyrazino[2,1-a]isoindole-6-one, 8-bromo-2-methyl-1,2,3,4,6,10b-hexahydropyrazino[2,1-a]isoindole-6-one, 8-hydroxy-2-methyl-1,2,3,4,6,10b-hexahydropyrazino[2,1-a]isoindole-6-one, 2,10b-dimethyl-1,2,3,4,6,10b-hexahydropyrazino[2,1-a]isoindole-6-one, 2,8-dimethyl-10b-propyl-1,2,3,4,6,10b-hexahydropyrazino[2,1-a]isoindole-6-one, 9-ethoxy-8-iodo-2-methyl-1,2,3,4,6,10b-hexahydropyrazino[2,1-a]isoindole-6-one, 10b-ethyl-2-methyl-4-trifluoromethyl-1,2,3,4,6,10b-hexahydropyrazino[2,1-a]isoindole-6-one, 4-ethyl-2-methyl-5-propyl-1,2,3,4,6,10b-hexahydropyrazino[2,1-a]isoindole-6-one, 9-butyl-2-methyl-1,2,3,4,6,10b-hexahydropyrazino[2,1-a]isoindole-6-one, 8-butoxy-2-methyl-10b-phenylmethyl-1,2,3,4,6,10b-hexahydropyrazino[2,1-a]isoindole-6-one, 2,3,3-trimethyl-1,2,3,4,6,10b-hexahydropyrazino[2,1-a]isoindole-6-one, 2,3-dimethyl-1,2,3,4,6,10b-hexahydropyrazino-[2,1-a]isoindole-6-one, 2,3,4-trimethyl-1,2,3,4,6,10b-hexahydropyrazino[2,1-a]isoindole-6-one, 5-methyl-1,2,3,4,4a,5,6,6a,11,12a-decahydroisoindolo[2,1-a]quinoxaline, 3,4-diethyl-2-methyl-1,2,3,4,6,10b-hexahydropyrazino-[2,1-a]isoindole-6-one and 2,3,3,4,4-pentamethyl-1,2,3,4,6,10b-hexahydropyrazino[2,1-a]isoindole-8-one.

EXAMPLE 14

2-Ethyl-1,2,3,4,6,10b-hexahydropyrazino[2,1-a]isoindol-6-one(Ia: R$^1$ and R$^2$ together form a ketone; R$^3$, R$^4$, R$^5$, R$^6$, R$^8$, R$^9$, R$^{10}$ and R$^{11}$=H, and R$^7$=Et)

A solution of 1,2,3,4,6,10b-hexahydropyrazino[2,1-a]isoindol-6-one (described in Example 8, 2.25 g, 0.01 mol) in 40 ml of benzene is added dropwise to a cold stirring mixture of sodium hydride (0.58 g of a 50% dispersion, 0.012 mol). The mixture is stirred at room temperature for 15 min and ethyl iodide (1.86 g, 0.01 mol) is added dropwise. The reaction is stirred at 50° C. for 18 hr and water is added. The organic phase is collected, washed with water, dried and evaporated to give the title compound (2.1 g), nmr (CDCl$_3$) δ 1.02(t), 2.44(q), 1.8–4.4(m), 4.45(d), 4.63(d) and 7.35–7.9(m).

The hydrobromide salt of the title compound is prepared as described in Example 7 and crystallized from ethanol, mp 304°–307° C., Anal. Calc'd. for C$_{13}$H$_{16}$N$_2$O.HBr: C, 52.53% H, 5.77% N, 9.43% and Found: C, 54.78% H, 6.73% N, 8.62%.

In the same manner but replacing the ethyl iodide with an equivalent amount of propyl bromide, butyl chloride, 2-methylbutyl iodide, pentyl bromide or 1,3-dimethylbutyl bromide, the following compounds of formula Ia are obtained, respectively: 2-propyl-1,2,3,4,6,10b-hexahydropyrazino[2,1-a]isoindol-6-one, 2-butyl-1,2,3,4,6,10b-hexahydropyrazino[2,1-a]isoindol-6-one, 2-(2-methylbutyl)-1,2,3,4,6,10b-hexahydropyrazino[2,1-a]isoindole-6-one, 2-pentyl-1,2,3,4,6,10b-hexahydropyrazino[2,1-a]isoindol-6-one, and 2-(1,3-dimethylbutyl)-1,2,3,4,6,10b-hexahydropyrazino[2,1-a]-isoindol-6-one.

EXAMPLE 15

2-(N,N-Dimethylaminoacetyl)-1,2,3,4,6,10b-hexahydropyrazino[2,1-a]isoindol-6-one (Ia: R$^1$ and R$^2$ together form a ketone; R$^3$, R$^4$, R$^5$, R$^6$, R$^8$, R$^9$, R$^{10}$ and R$^{11}$=H, and R$^7$=COCH$_2$NMe$_2$)

A solution of chloroacetyl chloride (657 mg, 0.0058 mol) in 30 ml of benzene is added dropwise to a stirring solution of 1,2,3,4,6,10b-hexahydropyrazino[2,1-a]isoindole-6-one (described in Example 8, 1.0 g, 0.0053 mol) and triethylamine (650 mg, 0.0064 mol) in 90 ml of benzene. The reaction is stirred at room temperature for 30 min and evaporated. A mixture of chloroform and water is added and the chloroform phase is collected, washed with water, dried and evaporated to afford 2-chloroacetyl-1,2,3,4,6,10b-hexahydropyrazino[2,1-a]isoindole-6-one, (1.2 g), nmr (CDCl$_3$) δ 3.0–3.5(m), 4.2–4.8(m) and 7.3–7.9(m).

A solution of the latter compound (3.4 g, 0.013 mol) in 150 ml of tetrahydrofuran and 42 ml of 40% aqueous dimethylamine is stirred at 40° C. for 18 hr. The reaction is evaporated and the residue is dissolved in a mixture of chloroform and water. The chloroform phase is collected, washed with water, dried, and evaporated to afford the title compound (3.2 g), nmr (CDCl$_3$) δ 2.4(s), 3.0–3.5(m), 4.2–4.7(m), 5.0–5.5(m) and 7.4–8.1(m).

The maleate salt of the title compound is prepared as described in Example 8 and crystallized from diethyl ether-ethanol, mp 182°–185° C., Anal. Calc'd. for C$_{15}$H$_{19}$N$_3$O$_2$·C$_4$H$_4$O$_4$: C, 58.60% H, 5.95% N, 10.79% and Found: C, 58.58% H, 5.87% N, 10.63.

In the same manner but replacing chloroacetyl chloride with an equivalent amount of 3-chloropropionyl chloride, 4-bromobutionyl bromide or 6-chlorohexionyl chloride, the following compounds of formula Ia are obtained, respectively: 2-[3-(dimethylamino)propionyl]-1,2,3,4,6,10b-hexahydropyrazino[2,1-a]isoindol-6-one, mp 89°–91° C., Anal. Calc'd. for C$_{16}$H$_{21}$N$_3$O$_2$: C, 66.87% H, 7.37% N, 14.62% and Found: C, 66.40% H, 7.44% N, 14.57%; 2-[4-(dimethylamino)butionyl]-1,2,3,4,6,10b-hexahydropyrazino[2,1-a]isoindol-6-one, and 2-[6-(dimethylamino)hexionyl]-1,2,3,4,6,10b-hexahydropyrazino-[2,1-a]isoindol-6-one.

Similarily by replacing dimethylamine with an equivalent amount of ethylamine, N-ethyl-N-methylamine, dipropylamine or N-butyl-N-ethylamine, the following compounds of formula Ia are obtained, respectively: 2-(N-ethylaminoacetyl)-1,2,3,4,6,10b-hexahydropyrazino[2,1-a]isoindol-6-one, 2-(N-ethyl-N-methylaminoacetyl)-1,2,3,4,6,10b-hexahydropyrazino[2,1-a]isoindol-6-one, 2-(N,N-dipropylaminoacetyl)-1,2,3,4,6,10b-hexahydropyrazino[2,1-a]isoindol-6-one and 2-(N-butyl-N-ethylaminoacetyl)-1,2,3,4,6,10b-hexahydropyrazino[2,1-a]isoindol-6-one.

EXAMPLE 16

N,N-Dimethyl-1,2,3,4,6,10b-hexahydropyrazino[2,1-a]isoindol-2-ethanamine (Ia: $R^1$, $R^2$, $R^3$, $R^4$, $R^5$, $R^6$, $R^8$, $R^9$, $R^{10}$ and $R^{11}$=H, and $R^7$=(CH$_2$)$_2$NMe$_2$)

A solution of 2-(N,N-dimethylaminoacetyl)-1,2,3,4,6,10b-hexahydropyrazino[2,1-a]isoindol-6-one (described in Example 15, 3.8 g, 0.014) in 110 ml of 1 M borane in tetrahydrofuran is refluxed with stirring for 18 hr. The reaction is cooled and water is added until foaming ceased, followed by 60 ml of 6 N hydrochloric acid. The reaction is distilled until the temperature at the distillation head is 90° C. The residue is made alkaline with 6 N sodium hydroxide and extracted with chloroform. The chloroform extract is washed with water, dried, and evaporated to afford the title compound, nmr (CDCl$_3$) δ2.25(s), 2.4–3.9(m), 4.1(d) and 7.1(m).

The dihydrobromide salt (2.4 g) of the title compound is prepared as described in Example 10 and crystallized from diethyl ether-ethanol, mp 266°–270° C., Anal. Calc'd. for C$_{15}$H$_{23}$N$_3$·2HBr: C, 44.24% H, 6.19% N, 10.32% and Found: C, 44.30% H, 6.21% N, 10.16%.

In the same manner but replacing 2-(N,N-dimethylaminoacetyl)-1,2,3,4,6,10b-hexahydropyrazino[2,1-a]isoindol-6-one with an equivalent amount of another compound of formula Ia, described in Example 15, the following compounds of formula Ia are obtained, respectively: N,N-dimethyl-1,2,3,4,6,10b-hexahydropyrazino[2,1-a]isoindol-2-propanamine, trihydrobromide salt, mp 268°–270° C., Anal. Calc'd. for C$_{16}$H$_{25}$N$_3$·3HBr: C, 38.26% H, 5.62% N, 8.37% and Found: C, 37.94% H, 5.56% N, 7.91%; N,N-dimethyl-1,2,3,4,6,10b-hexahydropyrazino[2,1-a]isoindol-2-butanamine; N,N-dimethyl-1,2,3,4,6,10b-hexahydropyrazino[2,1-a]isoindol-2-hexanamine; N-ethyl-1,2,3,4,6,10b-hexahydropyrazino[2,1-a]isoindol-2-propanamine; N-ethyl-N-methyl-1,2,3,4,6,10b-hexahydropyrazino[2,1-a]isoindol-2-propanamine, N,N-dipropyl-1,2,3,4,6,10b-hexahydropyrazino[2,1-a]isoindol-2-propanamine, and N-butyl-N-etyl-1,2,3,4,6,10b-hexahydropyrazino[2,1-a]isoindol-2-propanamine.

EXAMPLE 17

2-Ethyl-1,2,3,4,6,10b-hexahydropyrazino[2,1-a]isoindole (Ia: $R^1$, $R^2$, $R^3$, $R^4$, $R^5$, $R^6$, $R^8$, $R^9$, $R^{10}$ and $R^{11}$=H, and $R^7$=Et)

A solution of 2-acetyl-1,2,3,4,6,10b-hexahydropyrazino[2,1-a]isoindole (described in Example 12, 1.4 g, 0.0065 mol) in 6 ml of tetrahydrofuran is added dropwise to a cold stirring mixture of lithium aluminium hydride (1.4 g, 0.037 mol) in 15 ml of tetrahydrofuran. The reaction is stirred at room temperature for 18 hr. The excess hydride is destroyed by the cautious addition of water. The mixture is filtered and the filtrate is evaporated. The residue is dissolved in chloroform and the solution is washed with 5% sodium bicarbonate and water, dried and evaporated to give the title compound (1.2 g), nmr (CDCl$_3$) δ1.12(t), 2.52(q), 2.0–3.9(m), 3.72(d), 4.15(d) and 7.28(m).

The maleate salt (1.3 g) of the title compound is prepared as described in Example 8 and crystallized from diethyl ether-ethanol, mp 119°–122° C., Anal. Calc'd. for C$_{13}$H$_{18}$N$_2$·C$_4$H$_4$O$_4$: C, 64.13% H, 6.97% N, 8.80% and Found: C, 64.18% H, 7.28% N, 8.67%.

EXAMPLE 18

10b-Methyl-1,2,3,4,6,10b-hexahydropyrazino[2,1-a]isoindol-6-ol (Ia: $R^1$, $R^3$, $R^4$, $R^6$, $R^7$, $R^8$, $R^9$, $R^{10}$ and $R^{11}$=H; $R^2$=OH, and $R^5$=Me)

10b-Methyl-3,4-dihydropyrazino[2,1-a]isoindol-1,6(2H, 10bH)-dione (described in Example 6, 8.0 g, 0.037 mol) is added portionwise to a stirring mixture of lithium aluminium hydride (8.0 g, 0.21 mol) in 400 ml of tetrahydrofuran and the reaction is refluxed for 18 hr. After cooling, water is slowly added and the mixture is filtered. The filtrate is evaporated and the residue is dissolved in chloroform. The solution is washed with water, dried, and evaporated. The residue is chromatographed on silica gel using 80% methanol in chloroform and the eluates are evaporated to give the title compound (5.0 g), nmr (DMSO-d$_6$) δ1.48(s), 2.4–3.2(m), 4.2–5.6(m) and 7.0–7.5(m).

The dimaleate salt (5.1 g) of the title compound is prepared as described in Example 8 and crystallized from ethanol-diethyl ether, mp 128°–131° C., Anal. Calc'd. for C$_{12}$H$_{16}$N$_2$O·2C$_4$H$_4$O$_4$: C, 55.04% H, 5.54% N, 6.42% and Found: C, 54.98%, H, 5.51% N, 6.34%.

EXAMPLE 19

2-(4-Aminobenzoyl)-1,2,3,4,6,10b-hexahydropyrazino[2,1-a]isoindol-6-one (Ia: $R^1$ and $R^2$ together from a ketone; $R^3$, $R^4$, $R^5$, $R^6$, $R^8$, $R^9$, $R^{10}$ and $R^{11}$=H, and $R^7$=4-aminobenzoyl)

A mixture of 2-(4-nitrobenzoyl)-1,2,3,4,6,10b-hexahydropyrazino[2,1-a]isoindol-6-one (described in Example 12, 5.6 g, 0.0166 mol) and 5% palladium on carbon in ethanol (3200 ml) is rapidly stirred under an atmosphere of hydrogen at room temperature. The mixture is filtered through diatomaceous earth and the filtrate is evaporated. The residue is crystallized from methanol to give the title compound (2.7 g), mp 260°–262° C., Anal. Calc'd. for $C_{18}H_{17}N_3O_2$: C, 70.34% H, 5.58% N, 13.67% and Found: C, 70.36% H, 5.58% N, 13.57%.

EXAMPLE 20

6-Oxo-1,2,3,4,6,10b-hexahydropyrazino[2,1-a]isoindol-2-Acetic Acid (Ia: $R^1$ and $R^2$ together form a ketone; $R^3$, $R^4$, $R^5$, $R^6$, $R^8$, $R^9$, $R^{10}$ and $R^{11}$=H, and $R^7$=$CH_2COOH$)

A solution of 1,2,3,4,6,10b-hexahydropyrazino[2,1-a]isoindol-6-one (described in Example 8, 7.5 g, 0.04 mol) in 150 ml of benzene is added to sodium hydride (1.7 g of a 50% dispersion in mineral oil, 0.036 mol) in 200 ml of benzene and stirred at room temperature for 30 min. A solution of ethyl bromoacetate (8.8 g, 0.044 mol) in 150 ml of benzene is added and the reaction is refluxed with stirring for 3 hr and cooled. Water is cautiously added and the benzene layer is separated, washed with water, dried, and evaporated. The residue is chromatographed on silica gel using 50% acetone in benzene and the eluates are evaporated to give 6-oxo-1,2,3,4,6,10b-hexahydropyrazino[2,1-a]isoindole-1-acetic acid ethyl ester (5.5 g), nmr ($CDCl_3$) $\delta 1.3(t)$, 2.4–2.6(m), 2.8–3.5(m), 4.2(q), 4.6(m) and 7.3–7.7(m).

A solution of the latter compound (5.5 g, 0.02 mol) and sodium hydroxide (20 ml of 1 N solution) in 200 ml of ethanol is stirred at room temperature for 3 hr. The reaction is neutralized with 1 N hydrochloric acid and evaporated. Methanol is added and the mixture is filtered. The filtrate is evaporated to give the title compound (6.0 g). The title compound (6.0 g) is dissolved in ethanol (25 ml) and a solution of 40 ml of 2.75 N hydrogen chloride in ethanol is added. The precipitate is collected and crystallized from a mixture of methanol-water-diethyl ether to obtain the hydrochloride salt (4.0 g) of the title compound, mp 255°–260° C., Anal. Calc'd. for $C_{13}H_{14}N_2O_3.HCl$: C, 55.22% H, 5.35% N, 9.91% and Found: C, 54.92% H, 5.29% N, 9.75%.

EXAMPLE 21

2-(Cyclohexylcarbonyl)-1,2,3,4,6,10b-hexahydropyrazino[2,1-a]isoindol-6-one (Ia: $R^1$ and $R^2$ together form a ketone; $R^3$, $R^4$, $R^5$, $R^6$, $R^8$, $R^9$, $R^{10}$ and $R^{11}$=H, and $R^7$=cyclohexylcarbonyl)

A mixture of 3,4-dihydropyrazino[2,1-a]isoindole-1,6(2H, 10bH)-dione (6.0 g, 0.03 mol, described in Example 6) and cyclohexylcarbonyl chloride (6.5 g, 0.045 mol) is stirred at 120° C. for 6.5 hr and evaporated. The residue is chromatographed on silica gel using 20% acetone in benzene and the eluates are evaporated. The residue is crystallized from acetone to obtain 2-(cyclohexylcarbonyl)-1,2,3,4,6,10b-hexahydropyrazino[2,1-a]isoindole-1,6-dione (1.8 g), mp 167°–172° C., Anal. Calc'd. for $C_{18}H_{20}N_2O_3$: C, 69.21% H, 6.45% N, 8.97% and Found: C, 69.25% H, 6.47% N, 8.93%.

The latter compound is reduced with borane, in the same manner as described in Example 8, to obtain the title compound.

EXAMPLE 22

1,2,3,4,6,10b-Hexahydro-1-oxo-2-phenylmethyl-pyrazino[2,1-a]isoindole-6-carboxylic Acid Methyl Ester (IX; $R^5$, $R^8$, $R^9$, $R^{10}$, $R^{11}$, $R^{18}$ and $R^{19}$=H; $R^7$=phenylmethyl, and Alk=Me)

N-(Phenylmethyl)ethylene diamine (10.38 g) is added dropwise to a solution of $\alpha,\alpha'$-dibromo-1,2-benzenediacetic acid dimethyl ester [24 g, described by G. Cignarella and A. Vigevani, Gazz. Chim. Ital., 98, 1474 (1968)] in benzene (600 ml). The mixture is refluxed for 6 hr, cooled and filtered. The filtrate is evaporated and the residue is chromatographed on silica gel using diethyl ether-methanol (9:1). The appropriate fractions are evaporated to give isomer A (5.7 g) of the title compound, nmr ($CDCl_3$) $\delta 3.3(m)$, 3.8(s), 4.6(d), 4.92(d), 5.30(d) and 7.3–7.8(m). The eluant for the above chromatography is changed to methanol-diethyl ether (3:7) and the appropriate eluate fractions are evaporated to give isomer B (4.1 g) of the title compound, nmr ($CDCl_3$) $\delta 3.3(m)$, 3.8(s), 4.6(d), 4.92(d), 5.30(d) and 7.3–7.8(m).

EXAMPLE 23

1,3-Dihydro-2-[2-[N-(1,1-dimethylethoxycarbonyl)amino]ethyl]-2H-isoindole-1,3-dicarboxylic Acid Dimethyl Ester (VIII; $R^8$, $R^9$, $R^{10}$, $R^{11}$, $R^{18}$ and $R^{19}$=H; $R^{20}$=1,1-dimethylethoxycarbonyl and Alk=Me)

A solution of N-(1,1-dimethylethoxycarbonyl)-ethylene diamine (3 g) in benzene (25 ml) is added dropwise to a solution of $\alpha,\alpha'$-dibromo-1,2-benzenediacetic acid methyl ester (3.78 g) and triethylamine (3.5 g) in benzene (75 ml). The mixture is refluxed for 18 hr using a water separator condenser and filtered. The filtrate is evaporated and the residue is chromatographed on silica gel using diethyl ether-hexane-pyridine (500:500:1). The eluate is evaporated to give the title compound (1.7 g), nmr ($CDCl_3$) $\delta 1.4(s)$, 3.03(m), 3.63(s), 5.0(s) and 7.17(m).

EXAMPLE 24

1,2,3,4,6,10b-Hexahydro-1-oxo-pyrazino[2,1-a]isoindole-6-carboxylic Acid Methyl Ester (IX; $R^5$, $R^7$, $R^8$, $R^9$, $R^{10}$, $R^{11}$, $R^{18}$ and $R^{19}$=H, and Alk=Me)

A mixture of 1,3-dihydro-2-[2-[N-(1,1-dimethylethoxycarbonyl)amino]ethyl]-2H-isoindole-1,3-dicarboxylic acid dimethyl ester (1.5 g, described in Example 23), 25% hydrochloric acid (3 ml) and ethyl acetate (30 ml) is refluxed for 2 hr and evaporated. Water (20 ml) is added and the solution is extracted with chloroform. The chloroform extract is evaporated and the residue is chromatographed on silica gel using methanol-chloroform (1:49). The eluate is evaporated and the residue (0.45 g) is crystallized from dichloromethane-hexane to obtain the title compound, mp 165°–167° C.

EXAMPLE 25

1,2,3,4,6,10b-Hexahydro-6-hydroxymethyl-2-phenylmethyl-pyrazino[2,1-a]isoindole (Ia; $R^1$, $R^3$, $R^4$, $R^5$, $R^6$, $R^8$, $R^9$, $R^{10}$ and $R^{11}$=H, $R^2$=$CH_2OH$ and $R^7$=phenylmethyl)

A solution of isomer A of 1,2,3,4,6,10b-hexahydro-1-oxo-2-phenylmethylpyrazino[2,1-a]isoindole-6-carboxylic acid methyl ester (1.2 g, described in Example 22) in tetrahydrofuran (120 ml) and borane in tetrahydrofuran (1.0 molar, 10 ml) is refluxed for 24 hr and cooled to 0° C. A solution of 10% hydrochlorid acid is slowly added until the excess diborane is destroyed. The resulting mixture is refluxed for 30 min and evaporated. The residue is dissolved in water and the aqueous solution is extracted with diethyl ether. The resulting aqueous solution is basified with concentrated ammonium hydroxide, saturated with sodium chloride and extracted with chloroform. The organic extract is dried and evaporated. The residue is chromatographed on silica gel using diethyl ether and the appropriate eluate fractions are evaporated to give the title compound, nmr (CDCl$_3$) δ2.46(s), 1.66–3.4(m), 3.5(s), 4.5(m) and 7.35(m). The title compound is dissolved in diethyl ether and the solution is saturated with hydrogen chloride. The precipitate (0.70 g) is collected and crystallized from methanol-diethyl ether to give the hydrochloride salt of the title compound, mp 258°–259° C., Anal. Calc'd. for $C_{19}H_{26}N_2O\cdot HCl$: C, 62.12% H, 6.58% N, 7.63% and Found: C, 62.23% H, 6.54% N, 7.47%.

In the same manner but replacing isomer A of the starting material with isomer B (described in Example 22), the title compound is obtained.

EXAMPLE 26

1,2,3,4,6,10b-Hexahydro-6-hydroxymethyl-pyrazino[2,1-a]isoindole (Ia; $R^1$, $R^3$, $R^4$, $R^5$, $R^6$, $R^7$, $R^8$, $R^9$, $R^{10}$ and $R^{11}$=H and $R^2$=CH$_2$OH)

A mixture of 1,2,3,4,6,10b-hexahydro-1-oxopyrazino[2,1-a]isoindole-6-carboxylic acid methyl ester (0.5 g, described in Example 24) and lithium borohydride (0.044 g) in tetrahydrofuran (25 ml) is refluxed for 18 hr. Water is carefully added to decompose the excess hydride and the tetrahydrofuran is evaporated. Water is added and the solution is continuously extracted with ethyl acetate for 18 hr. The extract is dried and evaporated to give 1,2,3,4,6,10b-hexahydro-6-hydroxymethylpyrazino[2,1-a]isoindol-1-one (0.245 g), nmr (CDCl$_3$) δ2.8(s), 3.2(m), 3.75(m), 4.3(m), 4.9(m), 6.95(s) and 7.2(m).

The latter compound is reduced with borane, in the same manner as described in Example 25, to obtain the title compound.

EXAMPLE 27

1,3-Dihydro-3-(1-nitropropyl)-isobenzofuran-1-one (X; $R^6$=Et and $R^{18}$ and $R^{19}$=H)

A solution of sodium hydroxide (80 g) in water is added to a stirring suspension of 3-formyl-benzoic acid (150 g) and nitropropane (89 g) in water (400 ml). The temperature of the mixture is maintained between 0°–5° C. during the addition and the mixture is stirred at this temperature for 4 hr. The solution is acidified with conc. hydrochloric acid and extracted with benzene. The organic solution is washed with water and brine, dried and evaporated. The residue is chromatographed on silica gel using chloroform and the eluates are evaporated. The residue (170 g) is crystallized from methylene chloride-diethyl ether to obtain the title compound, mp 90°–92° C.

EXAMPLE 28

2-(2-Nitro-1-propenyl)-benzoic Acid Methyl Ester (XI; $R^6$=Me, and $R^{18}$ and $R^{19}$=H)

A mixture of 1,3-dihydro-3-(1-nitroethyl)-isobenzofuran-1-one [2.0 g, described by J. J. Stehle et al., J. Org. Chem., 10, 429 (1945)], dimethyl sulfate (1.6 ml) and potassium carbonate (2.4 g) in acetone (50 ml) is stirred at 25° C. for 18 hr under dry conditions. The mixture is filtered and the filtrate is evaporated. The residue is chromatographed on silica gel using benzene and the eluates are evaporated to give the title compound (1.672 g), nmr (CDCl$_3$) δ2.25(s), 3.91(s), 7.40(s), 7.60(m), 8.18(s) and 8.50(s).

In the same manner but replacing 1,3-dihydro-3-(1-nitroethyl)-isobenzofuran-1-one with an equivalent amount of 5-propyl-1,3-dihydro-3-(1-nitroethyl)-isobenzofuran-1-one, 6-methoxy-1,3-dihydro-3-(1-nitroethyl)-isobenzofuran-1-one, 6-bromo-1,3-dihydro-3-(1-nitroethyl)-isobenzofuran-1-one, 6-trifluoromethyl-1,3-dihydro-3-(1-nitroethyl)-isobenzofuran-1-one, 5-butoxy-1,3-dihydro-3-(1-nitroethyl)-isobenzofuran-1-one or 5-pentyl-1,3-dihydro-3-(1-nitroethyl)-isobenzofuran-1-one, the following compounds of formula XI are obtain, respectively: 5-propyl-2-(2-nitro-1-propenyl)-benzoic acid methyl ester, 4-methoxy-2-(2-nitro-1-propenyl)-benzoic acid methyl ester, 4-bromo-2-(2-nitro-1-propenyl)-benzoic acid methyl ester, 4-trifluoromethyl-2-(2-nitro-1-propenyl)-benzoic acid methyl ester, 5-butoxy-2-(2-nitro-1-propenyl)-benzoic acid methyl ester and 5-pentyl-2-(2-nitro-1-propenyl)-benzoic acid methyl ester.

EXAMPLE 29

2-(2-Nitro-1-butenyl)-benzoic Acid Methyl Ester (XI; $R^6$=Et, and $R^{18}$ and $R^{19}$=H)

A suspension of 1,3-dihydro-3-(1-nitropropyl)-isobenzofuran-1-one (53 g, described in Example 27), potassium carbonate (64 g) and dimethyl sulfate (45.4 g) in acetone (1.5 l) is stirred at room temperature for 18 hr and filtered. The filtrate is evaporated and the residue is chromatographed on silica gel using hexane-diethyl ether (4:1). The eluates are evaporated to give the title compound (49 g), nmr (CDCl$_3$) δ1.15(t), 2.65(q), 3.94(s), 7.55(m), 8.2(m) and 8.45(s).

EXAMPLE 30

2,3-Dihydro-2-(2,2-diethoxyethyl)-3-(1-nitroethyl)-isoindol-1-one (XIII; $R^6$=Et, and $R^{18}$ and $R^{19}$=H)

A mixture of 2-(2-nitro-1-propenyl)-benzoic acid methyl ester (1.6 g, described in Example 28), sodium acetate (1.1 g) and 2,2-diethoxyethanamine (1.25 ml) in acetonitrile (20 ml) is stirred at 25° C. for 18 hr and evaporated. The residue is dissolved in ethyl acetate. The organic solution is washed with 1 N hydrochloric acid and brine, dried and evaporated to give the title compound as a mixture of two isomers (2.5 g).

In the same manner but replacing 2-(2-nitro-1-propenyl)-benzoic acid methyl ester with an equivalent amount of another compound of formula XI, described in Example 28, the following compounds of formula XIII are obtained, respectively: 6-propyl-2,3-dihydro-2-(2,2-diethoxyethyl)-3-(1-nitroethyl)-isoindol-1-one, 5-methoxy-2,3-dihydro-2-(2,2-diethoxyethyl)-3-(1-nitroethyl)-isoindol-1-one, 5-bromo-2,3-dihydro-2-(2,2-diethoxyethyl)-3-(1-nitroethyl)-isoindol-1-one, 5-trifluoromethyl-2,3-dihydro-2-(2,2-diethoxyethyl)-3-(1-nitroethyl)-isoindol-1-one, 6-butoxy-2,3-dihydro-2-(2,2-diethoxyethyl)-3-(1-nitroethyl)-isoindol-1-one and 6-pentyl-2,3-dihydro-2-(2,2-diethoxyethyl)-3-(1-nitroethyl)-isoindol-1-one.

EXAMPLE 31

2,3-Dihydro-2-(2,2-diethoxyethyl)-3-(1-nitropropyl)-isoindol-1-one (XIII; $R^6$=Et, and $R^{18}$ and $R^{19}$=H)

A suspension of 2-(2-nitro-1-butenyl)-benzoic acid methyl ester (49 g, described in Example 29) sodium acetate (27.5 g) and 2,2-diethoxyethanamine (44 g) in acetonitrile (1000 ml) is stirred at 25° C. for 24 hr and filtered. The filtrate is evaporated and the residue is dissolved in chloroform. The organic solution is washed with water, 10% hydrochloric acid and brine, dried and evaporated to obtain the title compound as a mixture of isomers (67 g).

EXAMPLE 32

2,3-Dihydro-2-(2,2-diethoxyethyl)-3-(1-aminoethyl)-isoindol-1-one (XIV; $R^6$=Me, and $R^{10}$, $R^{11}$, $R^{18}$ and $R^{19}$=H)

A mixture of the two isomers of 2,3-dihydro-2-(2,2-diethoxyethyl)-3-(1-nitroethyl)-isoindol-1-one (2.5 g, described in Example 30) and 10% palladium on carbon (0.25 g) in acetic acid-water (4:1, 50 ml) is stirred under an atmosphere of hydrogen at 50 psi and 25° C. for 18 hr and filtered. The filtrate is evaporated and dissolved in 2% hydrochloric acid. The solution is washed with diethyl ether, basified to pH 9 with ammonium hydroxide and extracted with ethyl acetate. The organic extract is dried, evaporated and chromatographed on silica gel using acetone-benzene (2:3). Evaporation of the eluates gives isomer A (1.14 g) of the title compound, ir ($CHCl_3$) 1675, 1120 and 1050 cm$^{-1}$ and isomer B (0.88 g) of the title compound, ir ($CHCl_3$) 1675, 1120 and 1050 cm$^{-1}$.

In the same manner but replacing 2,3-dihydro-2-(2,2-diethoxyethyl)-3-(1-nitroethyl)-isoindol-1-one with an equivalent amount of another compound of formula XIII, described in Example 30, the following compounds of formula XIV are obtained, respectively; 6-propyl-2,3-dihydro-2-(2,2-diethoxyethyl)-3-(1-aminoethyl)-isoindol-1-one 5-methoxy-2,3-dihydro-2-(2,2-diethoxyethyl)-3-(1-aminoethyl)-isoindol-1-one, 5-bromo-2,3-dihydro-2-(2,2-diethoxyethyl)-3-(1-aminoethyl)-isoindol-1-one, 5-trifluoromethyl-2,3-dihydro-2-(2,2-diethoxyethyl)-3-(1-aminoethyl)-isoindol-1-one, 6-butoxy-2,3-dihydro-2-(2,2-diethoxyethyl)-3-(1-aminoethyl)-isoindol-1-one and 6-pentyl-2,3-dihydro-2-(2,2-diethoxyethyl)-3-(1-aminoethyl)-isoindol-1-one.

EXAMPLE 33

1-Methyl-1,2,3,4,6,10b-hexahydropyrazino[2,1-a]isoindol-6-one (Ia; $R^1$ and $R^2$ form a ketone; $R^3$, $R^4$, $R^5$, $R^7$, $R^8$, $R^9$, $R^{10}$ and $R^{11}$=H; and $R^6$=Me)

A mixture of isomer A of 2,3-dihydro-2-(2,2-diethoxyethyl)-3-(1-aminoethyl)-isoindol-1-one (1.13 g, described in Example 32) and 10% palladium on carbon (0.11 g) in methanol (40 ml) and 1 N hydrochloric acid (30 ml) is stirred under an atmosphere of hydrogen at 25° C. for 48 hr and filtered. The filtrate is neutralized with conc. ammonium hydroxide and the methanol in the solution is evaporated. The aqueous solution is brought to pH 9 with conc. ammonium hydroxide, saturated with sodium chloride and extracted with ethyl acetate. The extract is dried and evaporated to give isomer A of the title compound (0.648 g.) The latter compound is reacted with maleic acid, in the same manner as described in Example 7, to obtain the maleate salt (0.44 g) of isomer A of the title compound, crystallized from ethanol-diethyl ether, mp 181°–182° C., Anal. Calc'd. for $C_{12}H_{14}N_2O.C_4H_4O_4$: C, 60.37% H, 5.70% N, 8.80% and Found: C, 60.25% H, 5.68% N, 8.79%.

In the same manner but replacing isomer A of the starting material with an equivalent amount of isomer B, described in Example 32, isomer B of the title compound and the maleate salt of isomer B of the title compound, crystallized from ethanol, mp 190°–191° C., Anal. Calc'd. for $C_{12}H_{14}N_2O_4.C_4H_4O_4$: C, 60.37% H, 5.70% N, 8.80% and Found: C, 60.19% H, 5.64% N, 8.86%, are obtained.

Similarly, by replacing isomer A of 2,3-dihydro-2-(2,2-diethoxyethyl)-3-(1-aminoethyl)-isoindol-1-one with an equivalent amount of another compound of formula XIV, described in Example 32, the following compounds of formula Ia are obtained, respectively: 8-propyl-methyl-1,2,3,4,6,10b-hexahydropyrazino[2,1-a]isoindol-6-one, 9-methoxy-1-methyl-1,2,3,4,6,10b-hexahydropyrazino[2,1-a]isoindol-6-one, 9-bromo-1,2,3,4,6,10b-hexahydropyrazino[2,1-a]isoindol-6-one, 9-trifluoromethyl-1,2,3,4,6,10b-hexahydropyrazino[2,1-a]isoindol-6-one, 8-butoxy-1,2,3,4,6,10b-hexahydropyrazino[2,1-a]isoindol-6-one and 8-pentyl-1,2,3,4,6,10b-hexahydropyrazino[2,1-a]isoindol-6-one.

EXAMPLE 34

1-Ethyl-1,2,3,4,6,10b-hexahydropyrazino[2,1-a]isoindol-6-one (Ia; $R^1$ and $R^2$ form a ketone; $R^3$, $R^4$, $R^5$, $R^7$, $R^8$, $R^9$, $R^{10}$ and $R^{11}$=H; $R^6$=Et)

A mixture of 2,3-dihydro-2-(2,2-diethoxyethyl)-3-(1-nitropropyl)-isoindol-1-one (10.0 g, described in Example 31) and 10% palladium on carbon (1.0 g) in ethanol (100 ml) is stirred under an atmosphere of hydrogen at 50 psi and 70° C. and filtered. The filtrate is evaporated and dissolved in 1 N hydrochloric acid. The aqueous solution is washed with diethyl ether, brought to pH 9 with conc. ammonium hydroxide, saturated with sodium chloride and extracted with chloroform. The organic extract is dried, evaporated and chromatographed on silica gel using acetone-benzene (1:9). The eluates are evaporated to give isomer A (1.4 g) of the title compound. The latter compound is reacted with maleic acid, in the same manner as described in Example 7, to obtain the maleate salt (1.1 g) of isomer A of the title compound, crystallized from ethanol-diethyl ether, mp 168°–169° C., Anal. Calc'd. for $C_{13}H_{15}N_2O.C_4H_4O$: C, 61.44% H, 6.07% N, 8.43% and Found: C, 61.61% H, 6.19% N, 8.32%.

The eluate for the above chromatography is changed to acetone and the eluates are evaporated to give isomer B (1.0 g) of the title compound. The latter compound is reacted with maleic acid, in the same manner as described in Example 7, to obtain the maleate salt (0.50 g) of isomer B of the title compound, crystallized from ethanol-diethyl ether, mp 171°–173° C., Anal. Calc'd. for $C_{13}H_{15}N_2O.C_4H_4O_4$: C, 61.44% H, 6.07% N, 8.43% and Found: C, 61.21% H, 6.08% N, 8.32%.

EXAMPLE 35

1-Methyl-1,2,3,4,6,10b-hexahydropyrazino[2,1a]isoindole (Ia; $R^1$, $R^2$, $R^3$, $R^4$, $R^5$, $R^7$, $R^8$, $R^9$, $R^{10}$ and $R^{11}$=H and $R^6$=Me)

A solution of isomer A of 1-methyl-1,2,3,4,6,10;1 b-hexahydropyrazino[2,1-a]isoindol-6-one (0.55 g, described in Example 33) and a 1 molar solution of borane in tetrahydrofuran (13.6 ml) in tetrahydrofuran (41 ml) is refluxed overnight. Hydrochloric acid (10%) is slowly and carefully added until the solution reaches pH 2. The solution is distilled until the distillate reaches 90° C., basified with conc. ammonium hydroxide to pH 9 and extracted with chloroform. The organic extract is dried and evaporated to obtain isomer A (0.419 g) of the title compound. The latter compound is reacted with maleic acid, in the same manner as described in Example 7, to obtain the maleate salt of isomer A of the title compound, crystallized from ethanol-diethyl ether, mp 144°–145° C., Anal. Calc'd. for $C_{12}H_{16}N.C_4H_4O_4$: C, 63.14% H, 6.62% N, 9.21% and Found: C, 63.60% H, 6.54% N, 9.30%.

In the same manner but replacing isomer A of the starting material with an equivalent amount of isomer B (described in Example 33), isomer A or B of 1-ethyl-1,2,3,4,6,10b-hexahydropyrazino[2,1-a]isoindol-6-one (described in Example 34), the following compounds of formula Ia are obtained, respectively: isomer B of the title compound, the maleate salt thereof (crystallized from ethanol-diethyl ether, mp 135°–137° C., Anal. Calc'd. for $C_{12}H_{16}N.C_4H_4O_4$: C, 63.14% H, 6.62% H, 6.62% N, 9.21% and Found: C, 63.11% H, 6.71% N, 9.18%), isomer A of 1-ethyl-1,2,3,4,6,10b-hexahydropyrazino[2,1-a]isoindole, the hydrobromide salt thereof (crystallized from methanol-diethyl ether, mp 270° C. (dec), Anal. Calc'd. for $C_{13}H_{18}N_2.HBr$: C, 42.99% H, 5.27% N, 7.71% and Found: C, 43.02% H, 5.44% N, 7.56%) and isomer B of 1-ethyl-1,2,3,4,6,10b-hexahydropyrazino[2,1-a]isoindole.

Similarly, by replacing isomer A of 1-methyl-1,2,3,4,6,10-hexahydropyrazino[2,1-a]isoindol-6-one with an equivalent amount of another compound of formula Ia, described in Example 33, the following compounds of formula Ia are obtained, respectively: 8-propyl-1-methyl-1,2,3,4,6,10b-hexahydropyrazino[2,1-a]isoindole, 9-methoxy-1-methyl-1,2,3,4,6,10-b-hexahydropyrazino[2,1-a]isoindole, 9-bromo-1-methyl-1,2,3,4,6,10b-hexahydropyrazino[2,1-a]isoindole, 9-trifluoromethyl-1-methyl-1,2,3,4,6,10b-hexahydropyrazino[2,1-a]isoindole, 8-butoxy-1-methyl-1,2,3,4,6,10b-hexahydropyrazino[2,1-a]isoindole and 8-pentyl-1-methyl-1,2,3,4,6,10b-hexahydropyrazino[2,1-a]isoindole.

EXAMPLE 36

1,3,4,10b-Tetrahydro-2-methylpyrimido[6,1-a]isoindol-6(2H)-one (Ib: $R^3$, $R^4$, $R^{14}$, $R^{16}$ and $R^{17}$=H, and $R^{15}$=Me)

Methyl lithium (104 ml of 2.2 M in diethyl ether) is added dropwise to a solution of 2,3-dihydro-3-oxo-1H-isoindole-1-acetic acid (described by F. M. Rowe et al., J. Chem. Soc., 1098 (1936), 10 g, 0.0524 mol) dissolved in 600 ml of dry tetrahydrofuran with stirring at room temperature. The reaction is stirred for 3 hr and poured into 200 ml of cold 10% hydrochloric acid. Most of the tetrahydrofuran is removed by evaporation and the residue is extracted with chloroform. The chloroform extract is washed with 5% sodium bicarbonate and water, dried and evaporated. The residue is chromatographed on silica gel using 30% acetone in benzene and the eluates are evaporated. The residue (5 g) is crystallized from benzene-petroleum ether to obtain 2,3-dihydro-3-oxo-1H-isoindole-1-propane-2′-one, mp 140°–142° C., Anal. Calc'd. for $C_{11}H_{11}NO_2$: C, 69.82% H, 5.86% N, 7.4% and Found: C, 69.97% H, 5.95% N, 7.13%.

A mixture of the latter compound (10 g, 0.053 mol), 7.5 g of hydroxylamine hydrochloride and 9.16 of potassium hydroxide in 610 ml of ethanol and 110 ml of water is refluxed for 10 min. The reaction is cooled with ice and most of the ethanol is removed by evaporation. The aqueous solution is extracted with chloroform. The chloroform extract is washed with water, dried and evaporated to afford 2,3-dihydro-3-oxo-1H-isoindole-1-propane-2-one 2-oxime (8.4 g).

To the latter compound (8.46 g, 0.0415 mol) in 200 ml of ethanol is added 12.7 g of Nickel-Aluminum alloy and 212 ml of 2 N sodium hydroxide while cooling, keeping the temperature during the addition of the sodium hydroxide at 20°–30° C. The reaction is stirred vigorously at room temperature for 1.5 hr, filtered through diatomaceous earth. Most of the ethanol is removed by evaporation and the residue is extracted with chloroform. The chloroform extract is washed with water, dried and evaporated to afford a yellow solid of 2,3-dihydro-3-oxo-1H-isoindole-1-(α-methyl)ethylamine (5 g), mp 118°–120° C.

A solution of the latter compound (5.0 g, 0.0263 mol) and 2.5 ml of 37% aqueous formaldehyde in 62 ml of ethanol is refluxed for 2.5 hr. The reaction is evaporated to dryness and the residue is chromatographed on silica gel using 2% methanol in chloroform. The eluates are evaporated and the residue (5.3 g) is crystallized from benzenepetroleum ether to give the title compound, mp 120°–121° C., Anal. Calc'd. for $C_{12}H_{14}N_2O$: C, 71.26% H, 6.98% N, 13.85% and Found: C, 71.17% H, 6.98% N, 13.55%. The title compound is treated with a solution of hydrogen chloride in diethyl ether. The precipitate is collected and crystallized from ethanol-diethyl ether to obtain the hydrochloride salt (3.3 g) of the title compound, mp 275°–280° C., Anal. Calc'd. for $C_{12}H_{14}N_2O.HCl$: C, 60.37% H, 6.33% N, 11.74% and Found: C, 60.24% H, 6.33% N, 11.60%.

EXAMPLE 37

1,10b-Dihydro-2,2-dimethylpyrimido[6,1-a]isoindol-6(2H)-one (Ib: $R^3$ and $R^4$=H, $R^{14}$ and $R^{15}$=Me, and $R^{16}$ and $R^{17}$ together form an imine)

A solution of 2,3-dihydro-3-oxo-1H-isoindole-1-acetic acid (described by F. M. Rowe et al., supra, 130 g, 0.682 mol) in methanol (1300 ml) containing 6.5 g of p-toluenesulfonic acid is refluxed with stirring for 3.5 hr. Most of the methanol is evaporated and the residue is dissolved in chloroform. The solution is washed with 5% aqueous sodium bicarbonate and water, dried and evaporated. The residue (125 g) is crystallized from isopropanol to give methyl 2,3-dihydro-3-oxo-1H-isoindole-1-acetate, mp 136°–138° C.

A solution of the latter compound (7.2 g, 0.035 mol) in 250 ml of tetrahydrofuran is added dropwise to a solution of methyl magnesium iodide (prepared from magnesium, 4.11 g, 0.075 gram-atoms and methyl iodide, 23.8 g, 0.168 mole, in 200 ml of diethyl ether). The reaction is refluxed for 18 hr with stirring, cooled and poured into 350 ml of ice-cold 10% sulfuric acid. The solution is extracted with chloroform and the chloroform extract is washed with 5% aqueous sodium bicarbonate and water, dried and evaporated. The residue is crystallized from benzene to give 2,3-dihydro-3-(2-hydroxy-2-methylpropyl)-1H-isoindol-1-one, which also is known as 1,3-dihydro-3-(2-hydroxy-2-methylpropyl9-2H-isoindole-1-one, (4.8 g), mp 122°–123° C., Anal. Calc'd. for $C_{12}H_{15}NO_2$: C, 70.22% H, 7.37% N, 6.82% and Found: C, 70.11% H, 7.37% N, 6.96%.

A solution of the latter compound (11.0 g, 0.0586 mol) and sodium cyanide (5.4 g, 0.11 mol) in 75 ml of acetic acid is stirred at 60° C. while a solution of 121 g of sulfuric acid and 66 ml of acetic acid is added dropwise. When the addition is complete, the reaction is stirred at room temperature for 4 hr. The reaction is poured into ice-water (1000 ml) and the solution is extracted with chloroform. The chloroform extract is washed with 5% aqueous sodium bicarbonate and water, dried and evaporated. The residue is chromatographed on silica gel using 50% acetone in benzene and the eluates are evaporated to give 1,3,4,10b-tetrahydro-4-hydroxy-2,2-dimethylpyrimido[6,1-a]isoindol-6(2H)-one (5.5 g), nmr (CDCl$_3$) δ1.55(d), 1.7–2.8(m), 4.6–4.9(m), 6.5–6.7(m) and 7.3–8.3(m).

A mixture of the latter compound (3.0 g, 0.0129 mol) and 10 ml of thionyl chloride is refluxed with stirring for 2 hr and evaporated. The residue (2.5 g) is crystallized from isopropanol to give the hydrochloride salt (1.85 g) of the title compound, mp 285°–295° C. (dec), Anal. Calc'd. for C$_{13}$H$_{14}$N$_2$O.HCl: C, 62.29% H, 5.63% N, 11.18% Cl, 14.15% and Found: C, 61.92% H, 5.99% N, 11.13% Cl, 13.97%.

In the same manner but replacing 2,3-dihydro-3-oxo-1H-isoindole-1-acetic acid with a equivalent amount of 6-ethyl-2,3-dihydro-3-oxo-1H-isoindole-1acetic acid, 6-propoxy-2,3-dihydro-3-oxo-1H-isoindole-1-acetic acid, 5-trifluoromethyl-2,3-dihydro-3-oxo-1H-isoindole-1-acetic acid, 5-pentyl-2,3-dihydro-3-oxo-1H-isoindole-1-acetic acid or 6-bromo-2,3-dihydro-3-oxo-1H-isoindole-1-acetic acid, the following compounds of formula Ib are obtained, respectively: 9-ethyl-1,10b-dihydro-2,2-dimethylpyrimido[6,1-a]isoindole-6(2H)-one, 9-propoxy-1,10b-dihydro-2,2-dimethylpyrimido[6,1-a]isoindole-6(2H)-one, 8-trifluoromethyl-1,10-dihydro-2,2-dimethylpyrimido[6,1-a]isoindole-6(2H)-one, 8-pentyl-1,10b-dihydro-2,2-dimethylpyrimido[6,1-a]isoindole-6(2H)-one and 9-bromo-1,10b-dihydro-2,2-dimethylpyrimido[6,1-a]isoinol-6(2H)-one.

EXAMPLE 38

1,3,4,10b-Tetrahydro-2,2-Dimethylpyrimido[6,1-a]isoindol-6(2H)-one (Ib: R$^3$,R$^4$, R$^{16}$ and R$^{17}$=H, and R$^{14}$ and R$^{15}$=Me)

Sodium borohydride (4.4 g, 0.126 mol) is added portionwise to a stirring solution of 1,10b-dihydro-2,2-dimethylpyrimido[6,1-a]isoindol-6(2H)-one (described in Example 37, 8.0 g, 0.032 mol) in 150 ml of methanol. The mixture is refluxed for 1.5 hr and evaporated. Water is added and the solution is extracted with chloroform. The chloroform extract is washed with water, dried and evaporated. The residue is crystallized from benzene to give the title compound (6.9 g), mp 155°–156° C.

The title compound is treated with a solution of hydrogen chloride in diethyl ether. The precipitate is collected and crystallized from isopropanol to obtain the hydrochloride salt of the title compound, mp 303°–306° C., Anal. Calc'd. for C$_{13}$H$_{16}$N$_2$O.HCl: C, 61.77% H, 6.78% N, 11.08% Cl, 14.03% and Found: C, 61.81% H, 6.81% N, 11.06% Cl, 13.85%.

In the same manner but replacing 1,10b-dihydro-2,2-dimethylpyrimido[6,1-a]isoindol-6(2H)-one with an equivalent amount of another compound of formula Ib, described in Example 37, the following compounds of formula Ib are obtained, respectively: 9-ethyl-1,3,4,10b-tetrahydro-2,2-dimethylpyrimido[6,1-a]isoindole-6(2H)-one, 9-propoxy-1,3,4,10b-dihydro-2,2-dimethylpyrimido[6,1-a]isoindole-6(2H)-one, 8-trifluoromethyl-1,3,4,10b-dihydro-2,2-dimethylpyrimido[6,1-a]isoindole-6(2H)-one, 8-pentyl-1,3,4,10b-dihydro-2,2-dimethylpyrimido[6,1-a]isoindole-6(2H)-one and 9-bromo-1,3,4,10b-dihydro-2,2-dimethylpyrimido[6,1-a]isoindole-6(2H)-one.

EXAMPLE 39.

3-(N,N-Dimethylaminoacetyl)-1,3,4,10b-tetrahydro-2,2-dimethylpyrimido[6,1-a]isoindol-6(2H)-one (Ib: R$^3$,R$^4$ and R$^{17}$=H,R$^{14}$ and R$^{15}$=Me, and R$^6$=COCH$_2$NMe$_2$)

Bromoacetyl bromide (10.86 g, 0.0537 mol) in 100 ml of benzene is added dropwise to an ice-cold stirring mixture of 1,3,4,10b-tetrahydro-2,2-dimethylpyrimido-[6,1-a]isoindol-6(2H)-one hydrochloride (described in Example 38, 9.2 g, 0.0426 mol) and triethylamine (7.0 g, 0.0693 mol) in 500 ml of benzene. The reaction is stirred at room temperature for 18 hr and water is added. The organic phase is collected, washed with 5% hydrochloric acid, 5% sodium bicarbonate and water, dried and evaporated. The residue is chromatographed on silica gel using 30% acetone in benzene and the eluates are evaporated to give 3-(2-bromo-1-oxoethyl)-1,3,4,10b-tetrahydro-2,2-dimethylpyrimido[6,1-a]isoindol-6(2H)-one (9.9 g), nmr (CDCl$_3$) δ 1.5(s), 1.6(s), 2.0(m), 4.1(d), 4.7(d), 4.65(d), 5.85(d) and 7.7(m).

A solution of the latter compound (9.9 g, 0.0294 mol) in 600 ml of tetrahydrofuran is added dropwise to 100 ml of a stirring solution of 40% aqueous dimethylamine. The solution is stirred at 60° C. for 2 hr. Most of the tetrahydrofuran is removed by evaporation and water is added. The solution is extracted with chloroform and the chloroform extract is washed with 5% sodium bicarbonate and water, dried and evaporated to afford the title compound (9.8 g).

The maleate salt (7.6 g) of the title compound, prepared in the same manner as described in Example 7, melts at 156°–160° C., Anal. Calc'd. for C$_{17}$H$_{12}$N$_3$O$_2$.C$_4$H$_4$O$_4$: C, 60.42% H, 6.52% N, 10.07% and Found: C, 60.33% H, 6.49% N, 10.16%.

In the same manner but replacing dimethylamine with an equivalent amount of ethylamine, dibutylamine, N-ethyl-N-propylamine or pentylamine and replacing bromoacetyl bromide with an equivalent amount of 4-chlorobutionyl chloride, the following compounds of formula Ib are obtained, respectively: 3-[4-(ethylamino)-butionyl]-1,3,4,10b-tetrahydro-2,2-dimethylpyrimido[6,1-a]isoindol-6(2H)-one, 3-[4-(N,N-dibutylamino)- butionyl]-1,3,4,10b-tetrahydro-2,2-dimethylpyrimido[6,1a]isoindol6(2H)-one, 3-[4-(N-ethyl-N-propylamino)-butionyl]-1,3,4,10b-tetrahydro-2,2-dimethylpyrimido[6,1-a]isoindol-6(2H)-one and 3-[4-(pentylamino)-butionyl]-1,3,4,10b-tetrahydro-2,2-dimethylpyrimido[6,1-a]isoindol-6(2H)-one.

Similarly, by replacing 1,3,4,10b-tetrahydro-2,2-dimethylpyrimido[6,1-a]isoindol-6(2H)-one with an equivalent amount of another compound of formula Ib, described in Example 38, the following compounds of formula Ib are obtained, respectively: 9-ethyl-3-(N,N-dimethylaminoacetyl)-1,3,4,10b-tetrahydro-2,2-dimethylpyrimido[6,1-a]isoindol-6(2H)-one, 9-propoxyy-3-(N,N-dimethylaminoacetyl)-1,3,4,10b-tetrahydro-2,2-dimethylpyrimido[6,1-a]isoindol-6(2H)-one, 8-trifluoromethyl-3-(N,N-dimethylaminoacetyl)-1,3,4,10b-tetrahydro-2,2-dimethylpyrimido[6,1-a]isoindol-6(2H)one, 8-pentyl-3-(N,N-dimethylaminoacetyl)-

1,3,4,10b-tetrahydro-2,2-dimethylpyrimido[6,1-a]isoindol-6(2H)-one and 9-bromo-3-(N,N-dimethylaminoacetyl)-1,3,4,10b-tetrahydro-2,2-dimethylpyrimido[6,1-a]isoindol-6(2H)-one.

EXAMPLE 40

1,3,4,10b-Tetrahydropyrimido[6,1-a]isoindol-6(2H)-one
(Ib: $R^3, R^4, R^{14}, R^{15}, R^{16}$ and $R^{17}=H$)

A mixture of 3-cyyanomethylenephthalimidine (described by J. Kranz, Chem. Ber., 100, 2261 (1967), 19.2 g, 0.113 mol) and Raney nickel catalyst in ethanol saturated with ammonia is hydrogenated at 70° C. and 700 psi for 24 hr. The mixture is filtered and the filtrate is evaporated to give 3-aminoethyl-1-oxoisoindole, nmr (CDCl$_3$)δ 2.4(m), 3.0(m), 4.9(t) and 7.7(m). The hydrochloride salt (1.94 g) of the latter compound melts at 243°–248° C.

A solution of the latter salt (19.4 g, 0.0915 mol) and 37% aqueous formaldehyde (9 ml) in ethanol (320 ml) is refluxed for 2.5 hr and the ethanol is removed by evaporation. Aqueous sodium bicarbonate (5%) is added and the solution is extracted with chloroform. The chloroform extract is washed with water, dried and evaporated. The residue is chromatographed on silica gel using 10% methanol in chloroform and the eluates are evaporated to give the title compound (8.7 g).

The title compound is treated with a solution of hydrogen chloride in diethyl ether. The precipitate is collected and crystallized from isopropanol to obtain the hydrochloride salt of the title compound, mp 228°–235° C., Anal. Calc'd. for $C_{11}H_{11}N_2O.HCl$: C, 58.80% H, 5.83% N, 12.47% Cl, 15.78% and Found: C, 58.78% H, 6.15% N, 12.45% Cl, 15.89%.

We claim:

1. A compound of formula Ia

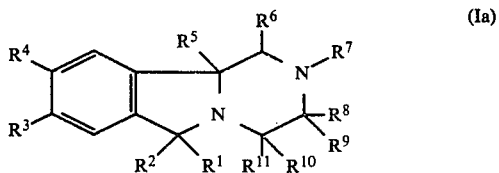

in which $R^1$ and $R^{11}$ are hydrogen; $R^2$ is hydrogen or hydroxymethyl; or $R^1$ and $R^2$ together form a ketone; $R^3$ and $R^4$ each is hydrogen, lower alkoxy, lower alkyl, halo or hydroxy; $R^5$ is hydrogen, lower alkyl or phenylmethyl; $R^6$ is hydrogen or lower alkyl; $R^7$ is hydrogen, lower alkyl, lower alkanoyl, cyclohexylcarbonyl, phenylmethyl, benzoyl, 4-nitrobenzoyl, 4-aminobenzoyl, a radical of formula $(CH_2)_nNR^{12}R^{13}$ wherein n is an integer from two to six, and $R^{12}$ and $R^{13}$ each is lower alkyl, or a radical of formula $CO-(CH_2)_{n-1}NR^{12}R^{13}$ wherein n, $R^{12}$ and $R^{13}$ are as defined herein; $R^8$, $R^9$ and $R^{10}$ each is hydrogen or lower alkyl, with the proviso that when $R^6$ is lower alkyl then $R^1$, $R^2$, $R^5$, $R^8$ and $R^9$ are hydrogen or $R^1$ and $R^2$ together form a ketone, or a therapeutically acceptable acid addition salt thereof.

2. 1,2,3,4,6,10b-Hexahydropyrazino[2,1-a]isoindole, as claimed in claim 1.

3. 8,9-Dimethoxy-1,2,3,4,6,10b-hexahydropyrazino[2,1-a]isoindole, as claimed in claim 1.

4. 8,9-Dichloro-1,2,3,4,6,10b-hexahydropyrazino[2,1-a]isoindole, as claimed in claim 1.

5. 9-Methoxy-1,2,3,4,6,10b-hexahydropyrazino[2,1-a]isoindole, as claimed in claim 1.

6. 8-Chloro-1,2,3,4,6,10b-hexahydropyrazino[2,1-a]isoindole, as claimed in claim 1.

7. 8-Methoxy-1,2,3,4,6,10b-hexahydropyrazino[2,1-a]isoindole, as claimed in claim 1.

8. 8-Bromo-1,2,3,4,6,10b-hexahydropyrazino[2,1-a]isoindole, as claimed in claim 1.

9. 8-Hydroxy-1,2,3,4,6,10b-hexahydropyrazino[2,1-a]isoindole, as claimed in claim 1.

10. 3,3-Dimethyl-1,2,3,4,6,10b-hexahydropyrazino[2,1-a]isoindole, as claimed in claim 1.

11. 3-Methyl-1,2,3,4,6,10b-hexahydropyrazino[2,1-a]isoindole, as claimed in claim 1.

12. 3,4-Dimethyl-1,2,3,4,6,10b-hexahydropyrazino[2,1-a]isoindole, as claimed in claim 1.

13. 2-Phenylmethyl-1,2,3,4,6,10b-hexahydropyrazino[2,1-a]isoindole, as claimed in claim 1.

14. 1,2,3,4,6,10b-Hexahydropyrazino[2,1-a]isoindole-6-one, as claimed in claim 1.

15. 8-Methoxy-1,2,3,4,6,10b-hexahydropyrazino[2,1-a]isoindol-6-one, as claimed in claim 1.

16. 3,3-Dimethyl-1,2,3,4,6,10b-hexahydropyrazino[2,1-a]isoindol-6-one, as claimed in claim 1.

17. 3-Methyl-1,2,3,4,6,10b-hexahydropyrazino[2,1-a]isoindol-6-one, as claimed in claim 1.

18. 3,4-Dimethyl-1,2,3,4,6,10b-hexahydropyrazino[2,1-a]isoindole-6-one, as claimed in claim 1.

19. 3,4-Dimethyl-1,2,3,4,6,10b-hexahydropyrazino[2,1-a]isoindol-6-one, whose maleate salt has mp 197°–198° C., as claimed in claim 1.

20. 3,4-Dimethyl-1,2,3,4,6,10b-hexahydropyrazino[2,1-a]isoindol-6-one, whose maleate salt has mp 170°–172° C., as claimed in claim 1.

21. 1,2,3,4,6,10b-Hexahydro-2-methylpyrazino[2,1-a]isoindole, as claimed in claim 1.

22. 10b-Phenylmethyl-1,2,3,4,6,10b-hexahydropyrazino[2,1-a]isoindole, as claimed in claim 1.

23. 2-Acetyl-1,2,3,4,6,10b-hexahydropyrazino[2,1-a]isoindol-6-one, as claimed in claim 1.

24. 2-Acetyl-1,2,3,4,6,10b-hexahydropyrazino[2,1-a]isoindole, as claimed in claim 1.

25. 2-(Cyclohexylcarbonyl)-1,2,3,4,6,10b-hexahydropyrazino[2,1-a]isoindol-6-one, as claimed in claim 1.

26. 2-(4-nitrobenzoyl)-1,2,3,4,6,10b-hexahydropyrazino[2,1-a]-isoindol-6-one, as claimed in claim 1.

27. 2-(Cyclohexylcarbonyl)-1,2,3,4,6,10b-hexahydropyrazino-[2,1-a]isoindole, as claimed in claim 1.

28. 2-Methyl-1,2,3,4,6,10b-hexahydropyrazino[2,1-a]isoindol-6-one, as claimed in claim 1.

29. 2-Ethyl-1,2,3,4,6,10b-hexahydropyrazino[2,1-a]isoindol-6-one, as claimed in claim 1.

30. 2-(N,N-Dimethylaminoacetyl)-1,2,3,4,6,10b-hexahydropyrazino[2,1-a]isoindol-6-one, as claimed in claim 1.

31. 2-[3-(Dimethylamino)propionyl]-1,2,3,4,6,10b-hexahydropyrazino[2,1-a]isoindol-6-one, as claimed in claim 1.

32. N,N-Dimethyl-1,2,3,4,6,10b-hexahydropyrazino[2,1-a]isoindol-2-ethanamine, as claimed in claim 1.

33. N,N-Dimethyl-1,2,3,4,6,10b-hexahydropyrazino[2,1-a]isoindol-2-propanamine, as claimed in claim 1.

34. 2-Ethyl-1,2,3,4,6,10b-hexahydropyrazino[2,1-a]isoindole, as claimed in claim 1.

35. 2-(4-Aminobenzoyl)-1,2,3,4,6,10b-hexahydropyrazino[2,1-a]isoindol-6-one, as claimed in claim 1.

36. 1,2,3,4,6,10b-Hexahydro-6-hydroxymethyl-2-phenylmethylpyrazino[2,1-a]isoindole, as claimed in claim 1.

37. 1-Methyl-1,2,3,4,6,10b-hexahydropyrazino[2,1-a]isoindole-6-one, as claimed in claim 1.

38. 1-Methyl-1,2,3,4,6,10b-hexahydropyrazino[2,1-a]isoindol-6-one, whose maleate salt has mp 181°–182° C., as claimed in claim 1.

39. 1-Methyl-1,2,3,4,6,10b-hexahydropyrazino[2,1-a]isoindol-6-one, whose maleate salt has mp 190°–191° C., as claimed in claim 1.

40. 1-Ethyl-1,2,3,4,6,10b-hexahydropyrazino[2,1-a]isoindole-6-one, as claimed in claim 1.

41. 1-Ethyl-1,2,3,4,6,10b-hexahydropyrazino[2,1-a]isodinol-6-one, whose maleate salt has mp 168°–169° C., as claimed in claim 1.

42. 1-Ethyl-1,2,3,4,6,10b-hexahydropyrazino[2,1-a]isoindol-6-one, whose maleate salt has mp 171°–173° C., as claimed in claim 1.

43. 1-Methyl-1,2,3,4,6,10b-hexahydropyrazino[2,1-a]isoindole, as claimed in claim 3.

44. 1-Methyl-1,2,3,4,6,10b-hexahydropyrazino[2,1-a]isoindole, whose maleate salt has mp 144°–145° C., as claimed in claim 1.

45. 1-Methyl-1,2,3,4,6,10b-hexahydropyrazino[2,1-a]isoindole, whose maleate salt has mp 135°–137.5° C., as claimed in claim 1.

46. 1-Ethyl-1,2,3,4,6,10b-hexahydropyrazino[2,1-b]isoindole, as claimed in claim 1.

47. 1-Ethyl-1,2,3,4,6,10b-hexahydropyrazino[2,1-a]isoindole, whose hydrobromide salt has mp 270° C. (dec.), as claimed in claim 1.

48. A method of treating hypertension in a mammal, which comprises administering to said mammal an effective antihypertensive amount of a compound of formula Ia or a therapeutically acceptable acid addition salt thereof, as claimed in claim 1.

49. An antihypertensive pharmaceutical composition, which comprises an effective amount of a compound of formula Ia or a therapeutically acceptable acid addition salt thereof, a claimed in claim 1, and a pharmaceutically acceptable carrier therefor.

50. A method of treating hypertension in an hypertensive mammal, which comprises administering to the mammal an antihypertensive effective amount of a compound of formula Ia of claim 1, or a therapeutically acceptable acid addition salt thereof, in combination with an effective amount of a diuretic and/or antihypertensive agent, in which the agent is chlorothiazide, hydrochlorothiazide or propranolol.

51. An antihypertensive pharmaceutical composition comprisng an effective amount of a compound of formula Ia of claim 1, or a therapeutically acceptable acid addition salt thereof, and a diuretic and/or antihypertensive agent, in which the agent is chlorothiazide, hydrochlorothiazide or propranolol.

52. The method of claim 50 in which the compound of formula Ia, or a therapeutically acceptable salt thereof, and the diuretic and/or antihypertensive agent is administered sequentially or simultaneously.

* * * * *